United States Patent
Kararli et al.

(10) Patent No.: US 7,172,769 B2
(45) Date of Patent: *Feb. 6, 2007

(54) CYCLOOXYGENASE-2 INHIBITOR COMPOSITIONS HAVING RAPID ONSET OF THERAPEUTIC EFFECT

(75) Inventors: Tugrul T. Kararli, Skokie, IL (US); Mark J. Kontny, Libertyville, IL (US); Subhash Desai, Wilmette, IL (US); Michael J. Hageman, Portage, MI (US); Royal J. Haskell, Kalamazoo, MI (US)

(73) Assignee: Pharmacia Corporation, St. Louis, MO (US)

( * ) Notice: Subject to any disclaimer, the term of this patent is extended or adjusted under 35 U.S.C. 154(b) by 467 days.

This patent is subject to a terminal disclaimer.

(21) Appl. No.: 10/031,898

(22) PCT Filed: Dec. 6, 2000
(Under 37 CFR 1.47)

(86) PCT No.: PCT/US00/32434

§ 371 (c)(1),
(2), (4) Date: Jul. 30, 2002

(87) PCT Pub. No.: WO01/41760

PCT Pub. Date: Jun. 14, 2001

(65) Prior Publication Data

US 2004/0265382 A1 Dec. 30, 2004

Related U.S. Application Data

(60) Provisional application No. 60/169,856, filed on Dec. 9, 1999.

(51) Int. Cl.
*A61K 9/50* (2006.01)
(52) U.S. Cl. .................................... 424/501; 424/489
(58) Field of Classification Search ............... 424/489, 424/501
See application file for complete search history.

(56) References Cited

U.S. PATENT DOCUMENTS 4,826,689 A  5/1989  Violanto et al.

(Continued)

FOREIGN PATENT DOCUMENTS

EC  98-2761  6/1999

(Continued)

OTHER PUBLICATIONS

The Merck Index, 12$^{th}$ Edition, Therapeutic Category and Biological Activity Index, lists therein headed "Analgesic", Anti-inflammatory and "Antipyretic", 1996.

*Primary Examiner*—Carlos A. Azpuru
(74) *Attorney, Agent, or Firm*—Patricia K. Fitzsimmons; Charles Ashbrook

(57) ABSTRACT

Pharmaceutical compositions are provided comprising one or more orally deliverable dose units, each comprising a selective cyclooxygenase-2 inhibitory drug of low water solubility in a therapeutically effective amount, wherein the drug is present in the form of solid particle, about 25% to 100% by weight of which are smaller than 1 μm. The compositions are useful in treatment or prophylaxis of cyclooxygenase-2 mediated conditions and disorders and have particular advantages where rapid onset of therapeutic effect is desired.

17 Claims, 3 Drawing Sheets

U.S. PATENT DOCUMENTS

| | | |
|---|---|---|
| 5,145,684 A | 9/1992 | Liversidge et al. |
| 5,298,262 A | 3/1994 | Na et al. |
| 5,302,401 A | 4/1994 | Liversidge et al. |
| 5,336,507 A | 8/1994 | Na et al. |
| 5,340,564 A | 8/1994 | Illig et al. |
| 5,344,991 A | 9/1994 | Reitz et al. |
| 5,346,702 A | 9/1994 | Na et al. |
| 5,352,459 A | 10/1994 | Hollister et al. |
| 5,354,560 A | 10/1994 | Lovrecich |
| 5,380,738 A | 1/1995 | Norman et al. |
| 5,384,124 A | 1/1995 | Courteille et al. |
| 5,393,790 A | 2/1995 | Reitz et al. |
| 5,401,765 A | 3/1995 | Lee |
| 5,418,254 A | 5/1995 | Huang et al. |
| 5,420,343 A | 5/1995 | Koszyk et al. |
| 5,429,824 A | 7/1995 | June |
| 5,434,178 A | 7/1995 | Talley et al. |
| 5,436,265 A | 7/1995 | Black et al. |
| 5,466,823 A | 11/1995 | Talley et al. |
| 5,474,995 A | 12/1995 | Ducharme et al. |
| 5,475,018 A | 12/1995 | Lee et al. |
| 5,486,534 A | 1/1996 | Lee et al. |
| 5,503,723 A | 4/1996 | Ruddy et al. |
| 5,510,118 A | 4/1996 | Bosch et al. |
| 5,510,368 A | 4/1996 | Lau et al. |
| 5,518,187 A | 5/1996 | Bruno et al. |
| 5,518,738 A | 5/1996 | Eickhoff et al. |
| 5,521,213 A | 5/1996 | Prasit et al. |
| 5,534,270 A | 7/1996 | De Castro |
| 5,536,508 A | 7/1996 | Canal et al. |
| 5,536,752 A | 7/1996 | Ducharme et al. |
| 5,543,297 A | 8/1996 | Cromlish et al. |
| 5,547,975 A | 8/1996 | Talley et al. |
| 5,550,142 A | 8/1996 | Ducharme et al. |
| 5,552,160 A | 9/1996 | Liversidge et al. |
| 5,552,422 A | 9/1996 | Gauthier et al. |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,783 A | 11/1996 | Desieno et al. |
| 5,580,579 A | 12/1996 | Ruddy et al. |
| 5,585,108 A | 12/1996 | Ruddy et al. |
| 5,585,504 A | 12/1996 | Desmond et al. |
| 5,587,143 A | 12/1996 | Wong |
| 5,591,456 A | 1/1997 | Franson et al. |
| 5,593,992 A | 1/1997 | Adams et al. |
| 5,596,008 A | 1/1997 | Lee |
| 5,604,253 A | 2/1997 | Lau et al. |
| 5,604,260 A | 2/1997 | Guay et al. |
| 5,616,458 A | 4/1997 | Lipsky et al. |
| 5,616,601 A | 4/1997 | Khanna et al. |
| 5,620,999 A | 4/1997 | Weier et al. |
| 5,622,938 A | 4/1997 | Wong |
| 5,633,272 A | 5/1997 | Talley et al. |
| 5,633,372 A | 5/1997 | Rajagopalan et al. |
| 5,639,780 A | 6/1997 | Lau et al. |
| 5,643,933 A | 7/1997 | Talley et al. |
| 5,658,903 A | 8/1997 | Adams et al. |
| 5,662,883 A | 9/1997 | Bagchi et al. |
| 5,665,331 A | 9/1997 | Bagchi et al. |
| 5,668,161 A | 9/1997 | Talley et al. |
| 5,670,510 A | 9/1997 | Huang et al. |
| 5,677,318 A | 10/1997 | Lau |
| 5,681,842 A | 10/1997 | Dellarie et al. |
| 5,686,460 A | 11/1997 | Nicolai et al. |
| 5,686,470 A | 11/1997 | Weier et al. |
| 5,696,143 A | 12/1997 | Talley et al. |
| 5,710,140 A | 1/1998 | Ducharme et al. |
| 5,716,955 A | 2/1998 | Adams et al. |
| 5,718,919 A | 2/1998 | Ruddy et al. |
| 5,723,485 A | 3/1998 | Gungor et al. |
| 5,739,166 A | 4/1998 | Reitz et al. |
| 5,741,798 A | 4/1998 | Lazer et al. |
| 5,747,001 A | 5/1998 | Wiedmann et al. |
| 5,756,499 A | 5/1998 | Adams et al. |
| 5,756,529 A | 5/1998 | Isakson et al. |
| 5,760,068 A | 6/1998 | Talley et al. |
| 5,776,967 A | 7/1998 | Kreft et al. |
| 5,783,597 A | 7/1998 | Beers et al. |
| 5,789,413 A | 8/1998 | Black et al. |
| 5,807,873 A | 9/1998 | Nicolai et al. |
| 5,817,700 A | 10/1998 | Dube et al. |
| 5,830,911 A | 11/1998 | Failli et al. |
| 5,849,943 A | 12/1998 | Atkinson et al. |
| 5,859,036 A | 1/1999 | Sartori et al. |
| 5,861,419 A | 1/1999 | Dube et al. |
| 5,866,596 A | 2/1999 | Sartori et al. |
| 5,869,524 A | 2/1999 | Failli |
| 5,869,660 A | 2/1999 | Adams et al. |
| 5,883,267 A | 3/1999 | Rossen et al. |
| 5,892,053 A | 4/1999 | Zhi et al. |
| 5,922,742 A | 7/1999 | Black et al. |
| 5,929,076 A | 7/1999 | Adams et al. |
| 5,932,598 A | 8/1999 | Talley et al. |
| 5,935,990 A | 8/1999 | Khanna et al. |
| 5,945,539 A | 8/1999 | Haruta et al. |
| 5,958,978 A | 9/1999 | Yamazaki et al. |
| 5,968,958 A | 10/1999 | Guay et al. |
| 5,972,950 A | 10/1999 | Nicolai et al. |
| 5,973,191 A | 10/1999 | Marnett et al. |
| 5,981,576 A | 11/1999 | Belley et al. |
| 5,994,381 A | 11/1999 | Haruta et al. |
| 6,002,014 A | 12/1999 | Haruta et al. |
| 6,004,960 A | 12/1999 | Li et al. |
| 6,005,000 A | 12/1999 | Hopper et al. |
| 6,020,343 A | 2/2000 | Belley et al. |
| 6,020,347 A | 2/2000 | DeLaszlo et al. |
| 6,034,256 A | 3/2000 | Carter et al. |
| 6,040,319 A | 3/2000 | Corley et al. |
| 6,040,450 A | 3/2000 | Davies et al. |
| 6,046,208 A | 4/2000 | Adams et al. |
| 6,046,217 A | 4/2000 | Friesen et al. |
| 6,054,455 A * | 4/2000 | Guess et al. ............ 514/231.2 |
| 6,057,319 A | 5/2000 | Black et al. |
| 6,063,804 A | 5/2000 | De Nanteuil et al. |
| 6,063,807 A | 5/2000 | Chabrier de Lassauniere et al. |
| 6,071,954 A | 6/2000 | LeBlanc et al. |
| 6,077,868 A | 6/2000 | Cook et al. |
| 6,077,869 A | 6/2000 | Sui et al. |
| 6,083,969 A | 7/2000 | Ferro et al. |
| 6,096,753 A | 8/2000 | Spohr et al. |
| 6,133,292 A | 10/2000 | Wang et al. |

FOREIGN PATENT DOCUMENTS

| | | |
|---|---|---|
| EP | 0 799 823 | 10/1987 |
| EP | 0 863 134 | 9/1996 |
| EP | 0 846 689 | 6/1998 |
| EP | 0 863 134 A1 | 9/1998 |
| EP | 0 985 666 | 3/2000 |
| WO | 93/25190 | 12/1993 |
| WO | 94/15932 | 7/1994 |
| WO | 96/19469 | 6/1996 |
| WO | 96/24336 | 8/1996 |
| WO | 96/26921 | 9/1996 |
| WO | 96/31509 | 10/1996 |
| WO | 96/36623 | 11/1996 |
| WO | 96/38418 | 12/1996 |
| WO | 97/10840 | 3/1997 |
| WO | 97/13767 | 4/1997 |
| WO | 97/14407 | 4/1997 |
| WO | 99/13755 | 4/1997 |

| | | | | | | |
|---|---|---|---|---|---|---|
| WO | 97/25048 | 7/1997 | | WO | 99/24404 | 5/1999 |
| WO | 97/30030 | 8/1997 | | WO | 99/25695 | 5/1999 |
| WO | 97/34882 | 9/1997 | | WO | 99/35130 | 7/1999 |
| WO | 97/46524 | 12/1997 | | WO | 98/41516 | 9/1999 |
| WO | 98/04527 | 2/1998 | | WO | 97/03953 | 12/1999 |
| WO | 98/06708 | 2/1998 | | WO | 99/61016 | 12/1999 |
| WO | 98/07425 | 2/1998 | | WO | 99/61436 | 12/1999 |
| WO | 98/17292 | 4/1998 | | WO | 99/62884 | 12/1999 |
| WO | 98/21195 | 5/1998 | | WO | 99/64415 | 12/1999 |
| WO | 98/22457 | 5/1998 | | WO | 99/65469 | 12/1999 |
| WO | 98/32732 | 7/1998 | | WO | 00/08024 | 2/2000 |
| WO | 98/35666 | 8/1998 | | WO | 00/10993 | 3/2000 |
| WO | 98/45294 | 9/1998 | | WO | 00/13684 | 3/2000 |
| WO | 98/43966 | 10/1998 | | WO | 00/18374 | 4/2000 |
| WO | 98/47871 | 10/1998 | | WO | 00/18741 | 4/2000 |
| WO | 99/01130 | 1/1999 | | WO | 00/18753 | 4/2000 |
| WO | 99/01131 | 1/1999 | | WO | 00/23426 | 4/2000 |
| WO | 99/01452 | 1/1999 | | WO | 00/24719 | 5/2000 |
| WO | 99/10331 | 3/1999 | | WO | 00/26216 | 5/2000 |
| WO | 99/10332 | 3/1999 | | WO | 00/27369 | 5/2000 |
| WO | 99/11605 | 3/1999 | | WO | 00/30615 | 6/2000 |
| WO | 99/12930 | 3/1999 | | WO | 00/31072 | 6/2000 |
| WO | 99/14195 | 3/1999 | | WO | WO 00/32189 | 6/2000 |
| WO | 99/14205 | 3/1999 | | WO | 00/40087 | 7/2000 |
| WO | 00/01380 | 4/1999 | | WO | 99/01455 | 7/2000 |
| WO | 99/15505 | 4/1999 | | WO | 00/56348 | 9/2000 |
| WO | WO 99/18960 | 4/1999 | | | | |
| WO | 99/23087 | 5/1999 | | * cited by examiner | | |

D1

D2

D3

D4

CYCLOOXYGENASE-2 INHIBITOR COMPOSITIONS HAVING RAPID ONSET OF THERAPEUTIC EFFECT

CROSS-REFERENCE TO RELATED APPLICATIONS

This application is a U.S. national stage application under 35 U.S.C. § 371 of the international application PCT/US00/32434, filed Dec. 6, 2000, which in turn claims priority to U.S. provisional patent application 60/169,856 filed Dec. 9, 1999. The entire text of each of the above patent applications is incorporated by reference into this application.

FIELD OF THE INVENTION

The present invention relates to orally deliverable pharmaceutical compositions containing a selective cyclooxygenase-2 inhibitory drug as an active ingredient, to processes for preparing such compositions, to methods of treatment of cyclooxygenase-2 mediated disorders comprising orally administering such compositions to a subject, and to use of such compositions in manufacture of medicaments.

BACKGROUND OF THE INVENTION

Numerous compounds have been reported having therapeutically and/or prophylactically useful selective cyclooxygenase-2 (COX-2) inhibitory effect, and have been disclosed as having utility in treatment or prevention of specific COX-2 mediated disorders or of such disorders in general. Among such compounds are a large number of substituted pyrazolyl benzenesulfonamides as reported in U.S. Pat. No. 5,760,068 to Talley et al., including for example the compound 4-[5-(4-methylphenyl)-3-(trifluoromethyl)-1H-pyrazol-1-yl]benzenesulfonamide, also referred to herein as celecoxib (I), and the compound 4-[5-(3-fluoro-4-methoxyphenyl)-3-difluoromethyl)-1H-pyrazol-1-yl]benzenesulfonamide, also referred to herein as deracoxib (II).

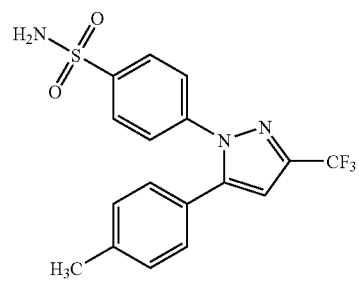

(I)

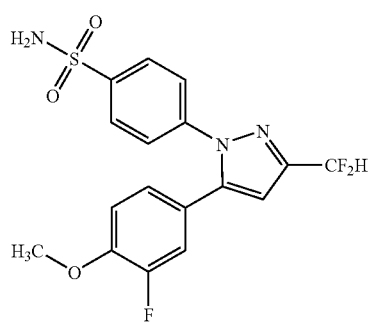

(II)

Other compounds reported to have therapeutically and/or prophylactically useful selective COX-2 inhibitory effect are substituted isoxazolyl benzenesulfonamides as reported in U.S. Pat. No. 5,633,272 to Talley et al., including the compound 4-[5-methyl-3-phenylisoxazol-4-yl]benzenesulfonamide, also referred to herein as valdecoxib (III).

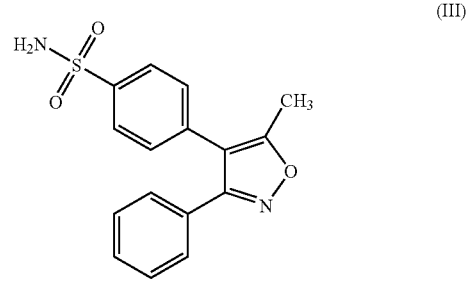

(III)

Still other compounds reported to have therapeutically and/or prophylactically useful selective COX-2 inhibitory effect are substituted (methylsulfonyl)phenyl furanones as reported in U.S. Pat. No. 5,474,995 to Ducharme et al., including the compound 3-phenyl-4-[4-(methylsulfonyl)phenyl]-5H-furan-2-one, also referred to herein as rofecoxib (IV).

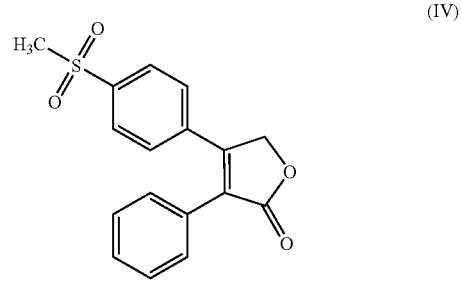

(IV)

U.S. Pat. No. 5,981,576 to Belley et al. discloses a further series of (methylsulfonyl)phenyl furanones said to be useful as selective COX-2 inhibitory drugs, including 3-(1-cyclopropylethoxy)-5,5-dimethyl-4-[4-(methylsulfonyl)phenyl]-5H-furan-2-one and 3-(1cyclopropylethoxy)-5,5-dimethyl-4-[4-(methylsulfonyl)phenyl]-5H-furan-2-one.

U.S. Pat. No. 5,861,419 to Dube et al. discloses substituted pyridines said to be useful as selective COX-2 inhibitory drugs, including for example the compound 5-chloro-3-(4-methylsulfonyl)phenyl-2-(2-methyl-5-pyridinyl)pyridine (V).

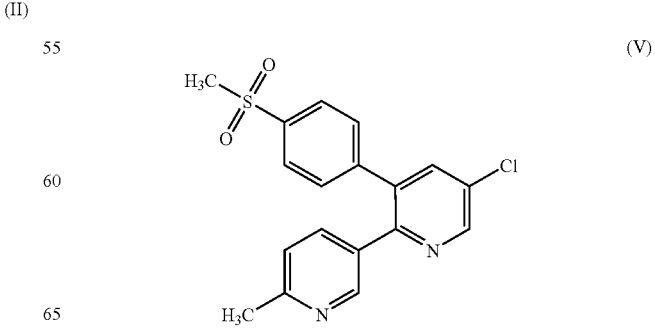

(V)

European Patent Application No. 0 863 134 discloses the compound 2-(3,5-difluorophenyl)-3-[4-(methylsulfonyl)phenyl]-2-cyclopoenten-1-one said to be useful as a selective COX-2 inhibitory drug.

U.S. Pat. No. 6,034,256 discloses a series of benzopyrans said to be useful as selective COX-2 inhibitory drugs, including the compound (S)-6,8-dichloro-2-(trifluoromethyl)-2H-1-benzopyran-3-carboxylic acid (VI).

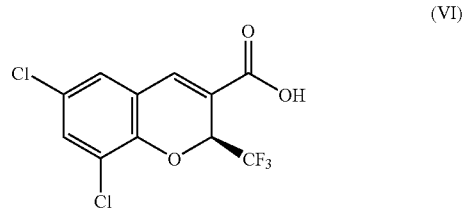

(VI)

Many selective COX-2 inhibitory drugs, including celecoxib, deracoxib, valdecoxib and rofecoxib, are hydrophobic and have low solubility in water. This has presented practical difficulties in formulating such drugs for oral administration, particularly where early onset of therapeutic effect is desired or required.

Illustratively, the formulation of celecoxib for effective oral administration to a subject has hitherto been complicated by the unique physical and chemical properties of celecoxib, particularly its low solubility and factors associated with its crystal structure, including cohesiveness, low bulk density and low compressibility. Celecoxib is unusually insoluble in aqueous media. Unformulated celecoxib is not readily dissolved and dispersed for rapid absorption in the gastrointestinal tract when administered orally, for example in capsule form. In addition, unformulated celecoxib, which has a crystal morphology that tends to form long cohesive needles, typically fuses into a monolithic mass upon compression in a tableting die. Even when blended with other substances, the celecoxib crystals tend to separate from the other substances and agglomerate together during mixing of the composition resulting in a non-uniformly blended composition containing undesirably large aggregates of celecoxib. Therefore, it is difficult to prepare a pharmaceutical composition containing celecoxib that has the desired blend uniformity. Further, handling problems arising for example from the low bulk density of celecoxib are encountered during preparation of celecoxib compositions. Accordingly, a need exists for solutions to numerous problems associated with preparation of compositions and dosage forms comprising celecoxib, particularly orally deliverable dose units.

Further, there exists an especial need for orally deliverable formulations of selective COX-2 inhibitory drugs of low water solubility including celecoxib, such formulations providing more rapid onset of therapeutic effect than the corresponding unformulated drugs or known formulations of these drugs. To the extent that rapid onset of therapeutic effect is related to pharmacokinetic parameters such as a high maximum blood serum concentration of the drug ($C_{max}$) and a short time from oral administration to reach such maximum blood serum concentration ($T_{max}$), there is an especial need for orally deliverable formulations of selective COX-2 inhibitory drugs of low water solubility including celecoxib, such formulations providing a greater $C_{max}$ and/or an earlier $T_{max}$ than the corresponding unformulated drugs or known formulations of these drugs.

As indicated hereinbelow, treatment with selective COX-2 inhibitory drugs including celecoxib is indicated or potentially indicated in a very wide array of COX-2 mediated conditions and disorders. It would be of benefit to provide formulations exhibiting pharmacokinetics consistent with rapid onset of therapeutic effect especially for treatment of acute disorders where early relief from pain or other symptoms is desired or required.

Such formulations would represent a significant advance in the treatment of COX-2 mediated conditions and disorders.

Selective COX-2 inhibitory drugs including celecoxib that are of low solubility in water are most conveniently formulated in solid particulate form. The individual or primary particles of the drug can dispersed in a liquid medium, as in a suspension formulation, or can be aggregated to form secondary particles or granules that can be encapsulated to provide a capsule dosage form, or compressed or molded to provide a tablet dosage form.

Numerous processes are known for preparing drug formulations having primary particle sizes in a desired range, or having a desired mean particle size, or having a particle size distribution characterized by a parameter such as $D_{90}$, which is defined herein as a linear measure of diameter having a value such that 90% by weight of particles in the formulation, in the longest dimension of the particles, are smaller than that diameter. Other particle size parameters used herein are defined in similar fashion; for example $D_{10}$, $D_{25}$ and $Ds_{50}$ parameters relate to linear measures of diameter having values such that 10%, 25% and 50% respectively by weight are smaller than that diameter.

For consistency with prior publications, the terms "microparticle" and "nanoparticle" are defined herein as in U.S. Pat. No. 5,384,124 to Courteille et al., to refer to particles having respectively a diameter of about 1 μm to about 2000 μm, and a diameter of less than about 1 μm (1000 nm). The preparation of microparticles and nanoparticles, according to U.S. Pat. No. 5,384,124, "is principally used to retard dissolution of active principles". However, U.S. Pat. No. 5,145,684 to Liversidge et al. discloses nanoparticulate compositions said to provide "unexpectedly high bioavailability" of drugs, particularly drugs having low solubility in a liquid medium such as water. International Publication No. WO 93/25190 provides pharmacokinetic data from a rat study indicating a higher apparent rate of absorption from oral administration of a nanoparticulate (average particle size 240–300 nm) than from oral administration of a microparticulate (particle size range 20–30 μm) dispersion of naproxen.

Numerous processes for preparation of nanoparticulate compositions of therapeutic agents are known. Typically these processes use mechanical means, such as milling, to reduce particle size to a nano (less than 1 μm) range, or precipitate nano-sized particles from solution.

SUMMARY OF THE INVENTION

According to the present invention, a poorly water soluble selective COX-2 inhibitory drug provides more rapid onset of therapeutic effect if, upon oral administration of a composition comprising the drug, the drug exhibits pharmacokinetic properties leading to a greater maximum blood serum concentration ($C_{max}$) and/or a shorter time following the administration to reach that maximum ($T_{max}$). It is contemplated that a greater $C_{max}$ and/or a shorter $T_{max}$ are obtained by reduction of size of solid particles comprising the drug such that a substantial portion by weight of the particles are smaller than about 1 μm in diameter, in the longest dimension of the particles. Without being bound by theory, it is believed that the greater $C_{max}$ and/or the shorter $T_{max}$ result from faster dissolution of the drug when particle size is reduced to less than about 1 μm.

Accordingly, there is now provided a pharmaceutical composition comprising one or more orally deliverable dose units, each comprising a selective COX-2 inhibitory drug of low water solubility in a therapeutically effective amount, wherein the drug is present in solid particles having a $D_{90}$ particle size of about 0.01 to about 200 μm, a sufficient portion by weight of the particles being smaller than 1 μm to provide a substantially higher $C_{max}$ and/or a substantially shorter $T_{max}$ by comparison with an otherwise similar composition wherein substantially all of the particles are larger than 1 μm.

There is also provided a pharmaceutical composition comprising one or more orally deliverable dose units, each comprising a selective COX-2 inhibitory drug of low water solubility in a therapeutically effective amount, wherein the drug is present in solid particles having a $D_{90}$ particle size of about 0.01 to about 200 μm, and wherein about 25% to 100% by weight of the particles are smaller than 1 μm.

The dose units comprising the composition can be in the form of discrete solid articles such as tablets, pills, hard or soft capsules, lozenges, sachets or pastilles; alternatively the composition can be in the form of a substantially homogeneous flowable mass, such as a particulate or granular solid or a liquid suspension, from which single dose units are measurably removable.

Also provided is a method of treating a medical condition or disorder in a subject where treatment with a COX-2 inhibitor is indicated, comprising orally administering one or more dose units of a composition of the invention one to about six times a day, preferably once or twice a day. Such a method is particularly useful where the medical condition or disorder is accompanied by acute pain.

Other features of this invention will be in part apparent and in part pointed out hereinafter.

DETAILED DESCRIPTION OF THE INVENTION

Figure 1:
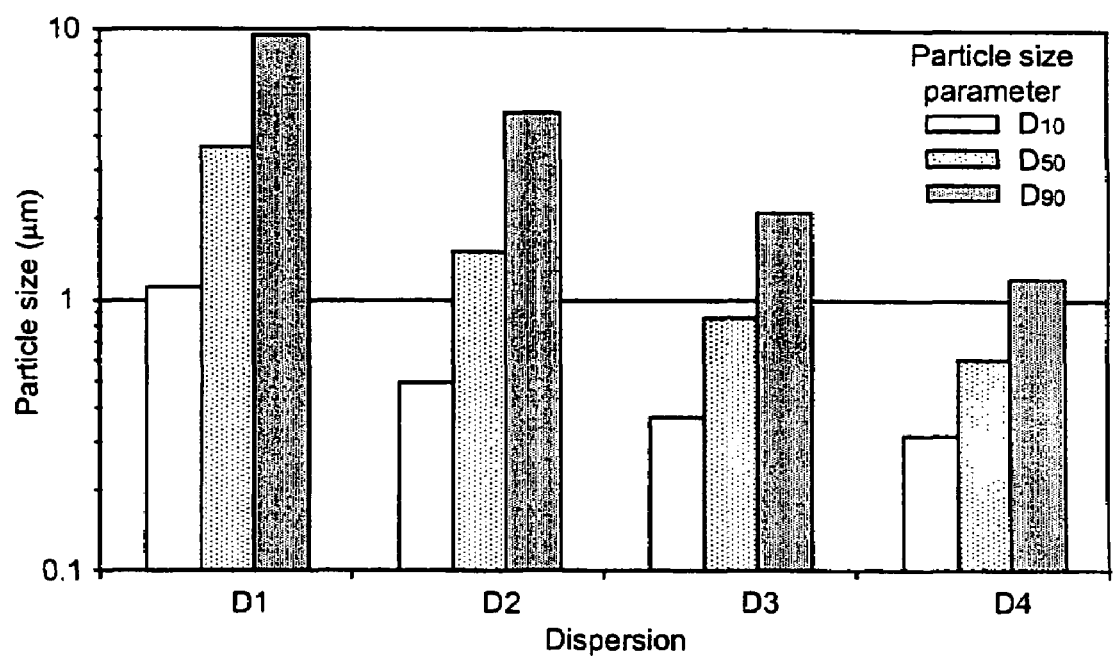
FIG. 1 presents particle size data for celecoxib dispersions D1–D4 prepared as described in Example 1, as measured by Fraunhofer diffraction.

Selective COX-2 inhibitory drugs for which the present invention is useful are drugs that inhibit COX-2 to a therapeutically useful degree while causing markedly less inhibition of cyclooxygenase-1 (COX-1) than conventional nonsteroidal anti-inflammatory drugs (NSAIDs).

The invention applies particularly to selective COX-2 inhibitory drugs of low water solubility, especially those having a solubility in distilled water at 25° C. lower than about 10 g/l, preferably lower than about 1 g/l.

The term "oral administration" herein includes any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. Absorption of the agent can occur in any part or parts of the gastrointestinal tract including the mouth, esophagus, stomach, duodenum, ileum and colon.

The term "orally deliverable" herein means suitable for oral administration.

The term "dose unit" herein means a portion of a pharmaceutical composition that contains an amount of a therapeutic agent, in the present case a selective COX-2 inhibitory drug, suitable for a single oral administration to provide a therapeutic effect. Typically one dose unit, or a small plurality (up to about 4) of dose units, administered as a single oral administration, provides a sufficient amount of the agent to result in the desired effect.

The term "present in solid particles" as applied to a selective COX-2 inhibitory drug herein encompasses compositions wherein the solid particles consist essentially of the drug and compositions where the solid particles comprise the drug in intimate mixture with one or more other ingredients. These other ingredients can include one or more therapeutic agents other than the selective COX-2 inhibitory drug and/or one or more pharmaceutically acceptable excipients.

The term "excipient" herein means any substance, not itself a therapeutic agent, used as a carrier or vehicle for delivery of a therapeutic agent to a subject or added to a pharmaceutical composition to improve its handling, storage, disintegration, dispersion, dissolution, release or organoleptic properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, lubricants, glidants, substances added to mask or counteract a disagreeable taste or odor, flavors, dyes, fragrances, and substances added to improve appearance of the composition.

The term "substantially homogeneous" with reference to a pharmaceutical composition that comprises several components means that the components are sufficiently mixed such that individual components are not present as discrete layers and do not form concentration gradients within the composition.

Compositions of the invention comprise one or more orally deliverable dose units. Each dose unit comprises a selective COX-2 inhibitory drug, illustratively celecoxib, in a therapeutically effective amount that is preferably about 10 mg to about 1000 mg.

It will be understood that a therapeutically effective amount of a selective COX-2 inhibitory drug for a subject is dependent inter alia on the body weight of the subject. Where the drug is celecoxib and the subject is a child or a small animal (e.g., a dog), for example, an amount of celecoxib relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of celecoxib are likely to require dose units containing a relatively greater amount of celecoxib. For an adult human, a therapeutically effective amount of celecoxib per dose unit in a composition of the present invention is typically about 50 mg to about 400 mg. Especially preferred amounts of celecoxib per dose unit are about 100 mg to about 200 mg, for example about 100 mg or about 200 mg.

For other selective COX-2 inhibitory drugs, an amount of the drug per dose unit can be in a range known to be therapeutically effective for such drugs. Preferably, the amount per dose unit is in a range providing therapeutic equivalence to celecoxib in the dose ranges indicated immediately above.

Dose units of celecoxib compositions of the invention typically contain about 10 mg to about 400 mg of celecoxib, for example, a 10, 20, 37.5, 50, 75, 100, 125, 150, 175, 200, 250, 300, 350 or 400 mg dose of celecoxib. Preferred dose units contain about 25 mg to about 400 mg of celecoxib. More preferred dose units contain about 50 mg to about 200 mg of celecoxib. A particular dose unit can be selected to accommodate the desired frequency of administration used to achieve a specified daily dosage. The amount of the unit dosage form of the composition that is administered and the dosage regimen for treating the condition or disorder will depend on a variety of factors, including the age, weight, sex and medical condition of the subject, the severity of the condition or disorder, the route and frequency of administration, and the particular selective COX-2 inhibitory drug selected, and thus may vary widely. One or more dose units can be administered up to about 6 times a day. It is contemplated, however, that for most purposes a once-a-day or twice-a-day administration regimen provides the desired therapeutic efficacy.

A composition of the invention preferably contains about 1% to about 95%, preferably about 10% to about 90%, more preferably about 25% to about 85%, and still more preferably about 30% to about 80%, by weight of the selective COX-2 inhibitory drug, alone or in intimate mixture with one or more excipients. The drug is at least partly in nanoparticulate form, i.e., in the form of solid particles of diameter less than 1 μm in the longest dimension of the particles.

The effects on pharmacokinetic properties of reducing particle size from the microparticle range (greater than 1 μm diameter) to the nanoparticle range are generally unpredictable for any particular drug or class of drugs. According to the present invention, for selective COX-2 inhibitory drugs of low water solubility, nanoparticulate compositions exhibit higher $C_{max}$ and/or shorter $T_{max}$ than microparticulate compositions. In one embodiment of the invention, therefore, the percentage by weight of the particles that are nanoparticles is sufficient to provide a substantially higher $C_{max}$ and/or a substantially shorter $T_{max}$ by comparison with an comparative composition wherein substantially all of the particles are larger than 1 μm. Preferably a composition of this embodiment has a sufficient percentage by weight of nanoparticles to provide a substantially shorter $T_{max}$, and more preferably a sufficient percentage by weight of nanoparticles to provide both a substantially higher $C_{max}$ and a substantially shorter $T_{max}$, than the comparative composition.

When administered orally to a fasting adult human, a celecoxib 100 mg dose unit preferably exhibits a $T_{max}$ of less than about 90 minutes, more preferably less than about 60 minutes and most preferably less than about 45 minutes, and a $C_{max}$ of at least about 100 ng/ml, more preferably at least about 200 ng/ml. Typically a celecoxib composition of the invention provides a blood serum concentration of celecoxib of at least about 50 ng/ml within 30 minutes of oral administration; preferred compositions achieve such a concentration in as little as 15 minutes. This early rise in blood serum concentration is believed to be associated with the rapid onset of therapeutic effect achieved by compositions of the present invention.

For selective COX-2 inhibitory drugs other than celecoxib, preferred compositions provide a minimum blood serum concentration of the drug that is therapeutically equivalent to the minimum celecoxib concentrations indicated immediately above.

In another embodiment of the invention, the selective COX-2 inhibitory drug, illustratively celecoxib, is present in solid particles having a $D_{90}$ particle size of about 0.01 to about 200 μm, wherein about 25% to 100% by weight of the particles are nanoparticles. Where the percentage by weight of nanoparticles is relatively low, for example about 25% to about 50%, preferably the $D_{90}$ particle size is about 0.01 to about 100 μm, more preferably about 0.01 to about 75 μm, still more preferably about 0.01 to about 40 μm, and even more preferably about 0.01 to about 25 μm. Particle size can vary continuously across the nanoparticulate and microparticulate range, or the composition can have a bimodal or multimodal particle size distribution, with one set of particles having a $D_{90}$ particle size less than 1 μm and another set of particles having a $D_{90}$ particle size substantially greater than 1 μm. It is generally preferred that at least about 50% by weight, and especially preferred that at least about 75% by weight, of the particles are nanoparticles. In one embodiment substantially all of the particles are smaller than 1 μm, i.e., the percentage by weight of nanoparticles is 100% or close to 100%.

Primary particles, generated for example by milling or grinding, or by precipitation from solution, can agglomerate to form secondary aggregate particles. The term "particle size" as used herein refers to size, in the longest dimension, of primary particles, unless the context demands otherwise.

In a preferred embodiment, a composition of the invention has a weight average particle size of about 100 nm to about 1000 nm, more preferably about 100 nm to about 900 nm, for example about 200 nm to about 400 nm, or about 500 nm to about 900 nm. The drug can be in crystalline or amorphous form in the nanoparticles. Processes for preparing nanoparticles that involve milling or grinding typically provide the drug in crystalline form, whereas processes that involve precipitation from solution frequently but not invariably provide the drug partly or wholly in amorphous form.

Compositions of the invention comprise a selective COX-2 inhibitory drug of low water solubility, for example celecoxib, partly or wholly in nanoparticulate form as described above, optionally together with one or more excipients selected from diluents, disintegrants, binding agents, wetting agents and lubricants. In one embodiment, nanoparticles comprising the drug have a surface modifying agent adsorbed on the surface thereof. In another embodiment, nanoparticles of the drug are contained in a matrix formed by a polymer. Preferably at least one of the excipients is a water soluble diluent or wetting agent. Such a water soluble diluent or wetting agent assists in the dispersion and dissolution of the drug when a composition of the invention is ingested. Preferably both a water soluble diluent and a wetting agent are present.

A composition of the invention can be a substantially homogeneous flowable mass such as a particulate or granular solid or a liquid, or it can be in the form of discrete articles such as capsules or tablets each comprising a single dose unit.

In a composition that is a substantially homogeneous flowable mass, single dose units are measurably removable using a suitable volumetric measuring device such as a spoon or cup. Suitable flowable masses include, but are not limited to, powders and granules. Alternatively, the flowable mass can be a suspension having the drug in a solid particulate phase dispersed in a liquid phase, preferably an aqueous phase. At least a portion of the particulate phase is nanoparticulate. In preparing such a suspension, use of a wetting agent such as polysorbate 80 or the like is likely to be beneficial. A suspension can be prepared by dispersing nanoparticulate or partially nanoparticulate drug in the liquid phase; alternatively the drug can be precipitated from solution in a solvent such as an alcohol, preferably ethanol. The aqueous phase preferably comprises a palatable vehicle such as water, syrup or fruit juice, for example apple juice.

The selective COX-2 inhibitory drug can be any such drug known in the art, including without limitation compounds disclosed in the patents and publications listed below, each of which is individually incorporated herein by reference.

U.S. Pat. No. 5,344,991 to Reitz & Li.
U.S. Pat. No. 5,380,738 to Norman et al.
U.S. Pat. No. 5,393,790 to Reitz et al.
U.S. Pat. No. 5,401,765 to Lee.
U.S. Pat. No. 5,418,254 to Huang & Reitz.
U.S. Pat. No. 5,420,343 to Koszyk & Weier.
U.S. Pat. No. 5,434,178 to Talley & Rogier.
U.S. Pat. No. 5,436,265 to Black et al.
Above-cited U.S. Pat. No. 5,466,823.
U.S. Pat. No. 5,474,995 to Ducharme et al.
U.S. Pat. No. 5,475,018 to Lee & Bertenshaw.
U.S. Pat. No. 5,486,534 to Lee et al.
U.S. Pat. No. 5,510,368 to Lau et al.
U.S. Pat. No. 5,521,213 to Prasit et al.
U.S. Pat. No. 5,536,752 to Ducharme et al.
U.S. Pat. No. 5,543,297 to Cromlish et al.
U.S. Pat. No. 5,547,975 to Talley et al.
U.S. Pat. No. 5,550,142 to Ducharme et al.
U.S. Pat. No. 5,552,422 to Gauthier et al.
U.S. Pat. No. 5,585,504 to Desmond et al.
U.S. Pat. No. 5,593,992 to Adams et al.
U.S. Pat. No. 5,596,008 to Lee.
U.S. Pat. No. 5,604,253 to Lau et al.
U.S. Pat. No. 5,604,260 to Guay & Li.
U.S. Pat. No. 5,616,458 to Lipsky et al.
U.S. Pat. No. 5,616,601 to Khanna et al.
U.S. Pat. No. 5,620,999 to Weier et al. Above-cited U.S. Pat. No. 5,633,272.
U.S. Pat. No. 5,639,780 to Lau et al.
U.S. Pat. No. 5,643,933 to Talley et al.
U.S. Pat. No. 5,658,903 to Adams et al.
U.S. Pat. No. 5,668,161 to Talley et al.
U.S. Pat. No. 5,670,510 to Huang & Reitz.
U.S. Pat. No. 5,677,318 to Lau.
U.S. Pat. No. 5,681,842 to Dellaria & Gane.
U.S. Pat. No. 5,686,460 to Nicolaï et al.
U.S. Pat. No. 5,686,470 to Weier et al.
U.S. Pat. No. 5,696,143 to Talley et al.
U.S. Pat. No. 5,710,140 to Ducharme et al.
U.S. Pat. No. 5,716,955 to Adams et al.
U.S. Pat. No. 5,723,485 to Güngör & Teulon.
U.S. Pat. No. 5,739,166 to Reitz et al.
U.S. Pat. No. 5,741,798 to Lazer et al.
U.S. Pat. No. 5,756,499 to Adams et al.
U.S. Pat. No. 5,756,529 to Isakson & Talley.
U.S. Pat. No. 5,776,967 to Kreft et al.
U.S. Pat. No. 5,783,597 to Beers & Wachter.
U.S. Pat. No. 5,789,413 to Black et al.
U.S. Pat. No. 5,807,873 to Nicolaï & Teulon.
U.S. Pat. No. 5,817,700 to Dube et al.
U.S. Pat. No. 5,830,911 to Failli et al.
U.S. Pat. No. 5,849,943 to Atkinson & Wang.
U.S. Pat. No. 5,859,036 to Sartori et al.
U.S. Pat. No. 5,861,419 to Dube et al.
U.S. Pat. No. 5,866,596 to Sartori & Teulon.
U.S. Pat. No. 5,869,524 to Failli.
U.S. Pat. No. 5,869,660 to Adams et al.
U.S. Pat. No. 5,883,267 to Rossen et al.
U.S. Pat. No. 5,892,053 to Zhi et al.
U.S. Pat. No. 5,922,742 to Black et al.
U.S. Pat. No. 5,929,076 to Adams & Garigipati.
U.S. Pat. No. 5,932,598 to Talley et al.
U.S. Pat. No. 5,935,990 to Khanna et al.
U.S. Pat. No. 5,945,539 to Haruta et al.
U.S. Pat. No. 5,958,978 to Yamazaki et al.
U.S. Pat. No. 5,968,958 to Guay et al.
U.S. Pat. No. 5,972,950 to Nicolaï & Teulon.
U.S. Pat. No. 5,973,191 to Marnett & Kalgutkar.
U.S. Pat. No. 5,981,576 to Belley et al.
U.S. Pat. No. 5,994,381 to Haruta et al.
U.S. Pat. No. 6,002,014 to Haruta et al.
U.S. Pat. No. 6,004,960 to Li et al.
U.S. Pat. No. 6,005,000 to Hopper et al.
U.S. Pat. No. 6,020,343 to Belley et al.
U.S. Pat. No. 6,020,347 to DeLaszlo & Hagmann.
U.S. Pat. No. 6,034,256 to Carter et al.
U.S. Pat. No. 6,040,319 to Corley et al.
U.S. Pat. No. 6,040,450 to Davies et al.
U.S. Pat. No. 6,046,208 to Adams et al.
U.S. Pat. No. 6,046,217 to Friesen et al.
U.S. Pat. No. 6,057,319 to Black et al.
U.S. Pat. No. 6,063,804 to De Nanteuil et al.
U.S. Pat. No. 6,063,807 to Chabrier de Lassauniere & Broquet.
U.S. Pat. No. 6,071,954 to LeBlanc et al.
U.S. Pat. No. 6,077,868 to Cook et al.
U.S. Pat. No. 6,077,869 to Sui & Wachter.
U.S. Pat. No. 6,083,969 to Ferro et al.
U.S. Pat. No. 6,096,753 to Spohr et al.
U.S. Pat. No. 6,133,292 to Wang et al.
International Patent Publication No. WO 94/15932.
International Patent Publication No. WO 96/19469.
International Patent Publication No. WO 96/26921.
International Patent Publication No. WO 96/31509.
International Patent Publication No. WO 96/36623.
International Patent Publication No. WO 96/38418.
International Patent Publication No. WO 97/03953.
International Patent Publication No. WO 97/10840.
International Patent Publication No. WO 97/13755.
International Patent Publication No. WO 97/13767.
International Patent Publication No. WO 97/25048.
International Patent Publication No. WO 97/30030.
International Patent Publication No. WO 97/34882.
International Patent Publication No. WO 97/46524.
International Patent Publication No. WO 98/04527.
International Patent Publication No. WO 98/06708.
International Patent Publication No. WO 98/07425.
International Patent Publication No. WO 98/17292.
International Patent Publication No. WO 98/21195.
International Patent Publication No. WO 98/22457.
International Patent Publication No. WO 98/32732.
International Patent Publication No. WO 98/41516.
International Patent Publication No. WO 98/43966.
International Patent Publication No. WO 98/45294.
International Patent Publication No. WO 98/47871.
International Patent Publication No. WO 99/01130.

International Patent Publication No. WO 99/01131.
International Patent Publication No. WO 99/01452.
International Patent Publication No. WO 99/01455.
International Patent Publication No. WO 99/10331.
International Patent Publication No. WO 99/10332.
International Patent Publication No. WO 99/11605.
International Patent Publication No. WO 99/12930.
International Patent Publication No. WO 99/14195.
International Patent Publication No. WO 99/14205.
International Patent Publication No. WO 99/15505.
International Patent Publication No. WO 99/23087.
International Patent Publication No. WO 99/24404.
International Patent Publication No. WO 99/25695.
International Patent Publication No. WO 99/35130.
International Patent Publication No. WO 99/61016.
International Patent Publication No. WO 99/61436.
International Patent Publication No. WO 99/62884.
International Patent Publication No. WO 99/64415.
International Patent Publication No. WO 00/01380.
International Patent Publication No. WO 00/08024.
International Patent Publication No. WO 00/10993.
International Patent Publication No. WO 00/13684.
International Patent Publication No. WO 00/18741.
International Patent Publication No. WO 00/18753.
International Patent Publication No. WO 00/23426.
International Patent Publication No. WO 00/24719.
International Patent Publication No. WO 00/26216.
International Patent Publication No. WO 00/31072.
International Patent Publication No. WO 00/40087.
International Patent Publication No. WO 00/56348.
European Patent Application No. 0 799 823.
European Patent Application No. 0 846 689.
European Patent Application No. 0 863 134.
European Patent Application No. 0 985 666.

Compositions of the invention are especially useful for compounds having the formula (VI):

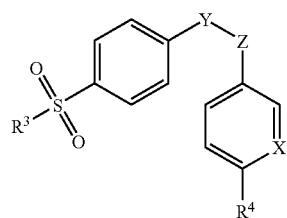

where $R^3$ is a methyl or amino group, $R^4$ is hydrogen or a $C_{1-4}$ alkyl or alkoxy group, X is N or $CR^5$ where $R^5$ is hydrogen or halogen, and Y and Z are independently carbon or nitrogen atoms defining adjacent atoms of a five- to six-membered ring that is unsubstituted or substituted at one or more positions with oxo, halo, methyl or halomethyl groups. Preferred such five- to six-membered rings are cyclopentenone, furanone, methylpyrazole, isoxazole and pyridine rings substituted at no more than one position.

Illustratively, compositions of the invention are suitable for celecoxib, deracoxib, valdecoxib, rofecoxib, 5-chloro-3-(4-methylsulfonyl)phenyl-2-(2-methyl-5-pyridinyl)pyridine, 2-(3,5-difluorophenyl)-3-[4-(methylsulfonyl)phenyl]-2-cyclopenten-1-one and (S)-6,8-dichloro-2-(trifluoromethyl)-2H-1-benzopyran-3-carboxylic acid, more particularly celecoxib and valdecoxib, and most particularly celecoxib.

The invention is illustrated herein with particular reference to celecoxib, and it will be understood that any other selective COX-2 inhibitory compound of low solubility in water can, if desired, be substituted in whole or in part for celecoxib in compositions herein described.

Compositions of the invention are useful in treatment and prevention of a very wide range of disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional nonsteroidal anti-inflammatory drugs (NSAIDs) that lack selectivity for COX-2 over COX-1. In particular, compositions of the invention have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Contemplated compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treatment of asthma, bronchitis, menstrual cramps, preterm labor, tendinitis, bursitis, allergic neuritis, cytomegalovirus infectivity, apoptosis including HIV-induced apoptosis, lumbago, liver disease including hepatitis, skin-related conditions such as psoriasis, eczema, acne, burns, dermatitis and ultraviolet radiation damage including sunburn, and post-operative inflammation including that following ophthalmic surgery such as cataract surgery or refractive surgery.

Such compositions are useful to treat gastrointestinal conditions such as inflammatory bowel disease, Crohn's disease, gastritis, irritable bowel syndrome and ulcerative colitis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of ophthalmic diseases, such as retinitis, conjunctivitis, retinopathies, uveitis, ocular photophobia, and of acute injury to the eye tissue.

Such compositions are useful in treatment of pulmonary inflammation, such as that associated with viral infections and cystic fibrosis, and in bone resorption such as that associated with osteoporosis.

Such compositions are useful for treatment of certain central nervous system disorders, such as cortical dementias including Alzheimer's disease, neurodegeneration, and central nervous system damage resulting from stroke, ischemia and trauma. The term "treatment" in the present context includes partial or total inhibition of dementias, including Alzheimer's disease, vascular dementia, multi-infarct dementia, pre-senile dementia, alcoholic dementia and senile dementia.

Such compositions are useful in treatment of allergic rhinitis, respiratory distress syndrome, endotoxin shock syndrome and liver disease.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures.

Such compositions are useful for treating and preventing inflammation-related cardiovascular disorders, including vascular diseases, coronary artery disease, aneurysm, vascular rejection, arteriosclerosis, atherosclerosis including cardiac transplant atherosclerosis, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries.

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis.

Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can also be used to treat fibrosis that occurs with radiation therapy. Such compositions can be used to treat subjects having adenomatous polyps, including those with familial adenomatous polyposis (FAP). Additionally, such compositions can be used to prevent polyps from forming in patients at risk of FAP.

Such compositions inhibit prostanoid-induced smooth muscle contraction by inhibiting synthesis of contractile prostanoids and hence can be of use in treatment of dysmenorrhea, premature labor, asthma and eosinophil-related disorders. They also can be of use for decreasing bone loss particularly in postmenopausal women (i.e., treatment of osteoporosis), and for treatment of glaucoma.

Preferred uses for compositions of the invention are for treatment of rheumatoid arthritis and osteoarthritis, for pain management generally (particularly post-oral surgery pain, post-general surgery pain, post-orthopedic surgery pain, and acute flares of osteoarthritis), for treatment of Alzheimer's disease, and for colon cancer chemoprevention.

For treatment of rheumatoid arthritis or osteoarthritis, compositions of the invention can be used to provide a daily dosage of celecoxib of about 50 mg to about 1000 mg, preferably about 100 mg to about 600 mg, more preferably about 150 mg to about 500 mg, still more preferably about 175 mg to about 400 mg, for example about 200 mg. A daily dose of celecoxib of about 0.7 to about 13 mg/kg body weight, preferably about 1.3 to about 8 mg/kg body weight, more preferably about 2 to about 6.7 mg/kg body weight, and still more preferably about 2.3 to about 5.3 mg/kg body weight, for example about 2.7 mg/kg body weight, is generally appropriate when administered in a composition of the invention. The daily dose can be administered in one to about four doses per day, preferably one or two doses per day.

For treatment of Alzheimer's disease or cancer, compositions of the invention can be used to provide a daily dosage of celecoxib of about 50 mg to about 1000 mg, preferably about 100 mg to about 800 mg, more preferably about 150 mg to about 600 mg, and still more preferably about 175 mg to about 400 mg, for example about 400 mg. A daily dose of about 0.7 to about 13 mg/kg body weight, preferably about 1.3 to about 10.7 mg/kg body weight, more preferably about 2 to about 8 mg/kg body weight, and still more preferably about 2.3 to about 5.3 mg/kg body weight, for example about 5.3 mg/kg body weight, is generally appropriate when administered in a composition of the invention. The daily dose can be administered in one to about four doses per day, preferably one or two doses per day.

For pain management, compositions of the invention can be used to provide a daily dosage of celecoxib of about 50 mg to about 1000 mg, preferably about 100 mg to about 600 mg, more preferably about 150 mg to about 500 mg, and still more preferably about 175 mg to about 400 mg, for example about 200 mg. A daily dose of celecoxib of about 0.7 to about 13 mg/kg body weight, preferably about 1.3 to about 8 mg/kg body weight, more preferably about 2 to about 6.7 mg/kg body weight, and still more preferably about 2.3 to about 5.3 mg/kg body weight, for example about 2.7 mg/kg body weight, is generally appropriate when administered in a composition of the invention. The daily dose can be administered in one to about four doses per day. Administration at a rate of one 50 mg dose unit four times a day, one 100 mg dose unit or two 50 mg dose units twice a day or one 200 mg dose unit, two 100 mg dose units or four 50 mg dose units once a day is preferred.

For selective COX-2 inhibitory drugs other than celecoxib, appropriate doses can be selected by reference to the patent literature cited hereinabove.

Besides being useful for human treatment, compositions of the invention are useful for veterinary treatment of companion animals, exotic animals, farm animals, and the like, particularly mammals. More particularly, compositions of the invention are useful for treatment of COX-2 mediated disorders in horses, dogs and cats.

The present invention is further directed to a therapeutic method of treating a condition or disorder where treatment with a COX-2 inhibitory drug is indicated, the method comprising oral administration of a composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

The present compositions can be used in combination therapies with opioids and other analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise use of a composition of the invention with one or more compounds selected from aceclofenac, acemetacin, e-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflurmic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see *The Merck Index,* 12th Edition, Therapeutic Category and Biological Activity Index, ed. S. Budavari (1996), pp. Ther-2 to Ther-3 and Ther-12 (Analgesic (Dental), Analgesic (Narcotic), Analgesic (Non-narcotic), Anti-inflammatory (Nonsteroidal))).

Particularly preferred combination therapies comprise use of a composition of the invention with an opioid compound, more particularly where the opioid compound is codeine, meperidine, morphine or a derivative thereof.

A celecoxib composition of the invention can also be administered in combination with a second selective COX-2 inhibitory drug, for example valdecoxib, rofecoxib, etc.

The compound to be administered in combination with celecoxib can be formulated separately from the celecoxib or co-formulated with the celecoxib in a composition of the invention. Where celecoxib is co-formulated with a second drug, for example an opioid drug, the second drug can be formulated in immediate-release, rapid-onset, sustained-release or dual-release form.

Nanoparticles comprising or consisting essentially of a selective COX-2 inhibitory drug of low water solubility can be prepared according to any process previously applied to preparation of other poorly water soluble drugs in nanoparticulate form. Suitable processes, without restriction, are illustratively disclosed for such other drugs in patents and publications listed below and incorporated herein by reference.

U.S. Pat. No. 4,826,689 to Violanto & Fischer.
Above-cited U.S. Pat. No. 5,145,684.
U.S. Pat. No. 5,298,262 to Na & Rajagopalan.
U.S. Pat. No. 5,302,401 to Liversidge et al.
U.S. Pat. No. 5,336,507 to Na & Rajagopalan.
U.S. Pat. No. 5,340,564 to Illig & Sarpotdar.
U.S. Pat. No. 5,346,702 to Na & Rajagopalan.
U.S. Pat. No. 5,352,459 to Hollister et al.
U.S. Pat. No. 5,354,560 to Lovrecich. Above-cited U.S. Pat. No. 5,384,124.
U.S. Pat. No. 5,429,824 to June.
U.S. Pat. No. 5,503,723 to Ruddy et al.
U.S. Pat. No. 5,510,118 to Bosch et al.
U.S. Pat. No. 5,518,187 to Bruno et al.
U.S. Pat. No. 5,518,738 to Eickhoff et al.
U.S. Pat. No. 5,534,270 to De Castro.
U.S. Pat. No. 5,536,508 to Canal et al.
U.S. Pat. No. 5,552,160 to Liversidge et al.
U.S. Pat. No. 5,560,931 to Eickhoff et al.
U.S. Pat. No. 5,560,932 to Bagchi et al.
U.S. Pat. No. 5,565,188 to Wong et al.
U.S. Pat. No. 5,569,448 to Wong et al.
U.S. Pat. No. 5,571,536 to Eickhoff et al.
U.S. Pat. No. 5,573,783 to Desieno & Stetsko.
U.S. Pat. No. 5,580,579 to Ruddy et al.
U.S. Pat. No. 5,585,108 to Ruddy et al.
U.S. Pat. No. 5,587,143 to Wong.
U.S. Pat. No. 5,591,456 to Franson et al.
U.S. Pat. No. 5,622,938 to Wong.
U.S. Pat. No. 5,662,883 to Bagchi et al.
U.S. Pat. No. 5,665,331 to Bagchi et al.
U.S. Pat. No. 5,718,919 to Ruddy et al.
U.S. Pat. No. 5,747,001 to Wiedmann et al.
Above-cited International Patent Publication No. WO 93/25190.
International Patent Publication No. WO 96/24336.
International Patent Publication No. WO 97/14407.
International Patent Publication No. WO 98/35666.
International Patent Publication No. WO 99/65469.
International Patent Publication No. WO 00/18374.
International Patent Publication No. WO 00/27369.
International Patent Publication No. WO 00/30615.

One of ordinary skill in the art will readily adapt the processes therein described to preparation of a poorly water soluble selective COX-2 inhibitory drug in nanoparticulate form.

In one embodiment of the invention, nanoparticles of a selective COX-2 inhibitory drug are prepared by a milling process, preferably a wet milling process in presence of a surface modifying agent that inhibits aggregation and/or crystal growth of nanoparticles once created. In another embodiment of the invention, nanoparticles of a selective COX-2 inhibitory drug are prepared by a precipitation process, preferably a process of precipitation in an aqueous medium from a solution of the drug in a non-aqueous solvent. The non-aqueous solvent can be a liquefied, e.g., supercritical, gas under pressure. Illustrative examples of these and other processes for preparing nanoparticles of a selective COX-2 inhibitory drug are presented with greater particularity below.

In one particular embodiment of the invention, nanoparticles are prepared by a process comprising the steps of (a) dispersing a selective COX-2 inhibitory drug and a surface modifying agent in a liquid dispersion medium; and (b) wet milling the resulting drug dispersion in presence of grinding media to result in crystalline nanoparticles of the drug having the surface modifying agent adsorbed on the surface thereof in an amount sufficient to maintain a weight average particle size of less than about 400 nm, substantially as disclosed in above-cited U.S. Pat. No. 5,145,684. The surface modifying agent inhibits aggregation of the nanoparticles and can be any of various polymers, low molecular weight oligomers, natural products, surfactants, etc. The nanoparticles in this and related embodiments are referred to herein as being composed of a nanocrystalline drug/surface modifier complex.

In a related embodiment of the invention, a nanocrystalline drug/surface modifier complex prepared as described above comprises a purified surface modifying agent, for example a purified polymeric surfactant, to prevent particle aggregation during a subsequent sterilization step, substantially as disclosed in above-cited U.S. Pat. No. 5,352,459.

In another related embodiment of the invention, a nanocrystalline drug/surface modifier complex prepared as described above comprises as a surface modifying agent the surfactant p-isononylphenoxypoly(glycidol), substantially as disclosed in above-cited U.S. Pat. No. 5,340,564.

In another related embodiment of the invention, a nanocrystalline drug/surface modifier complex prepared as described above is associated with an anionic or cationic cloud point modifier to increase the cloud point of the surface modifying agent, substantially as described in above-cited U.S. Pat. No. 5,298,262 (cationic or anionic surfactant as cloud point modifier), U.S. Pat. No. 5,336,507 (charged phospholipid as cloud point modifier), or U.S. Pat. No. 5,346,702 (non-ionic cloud point modifier).

In another related embodiment of the invention, a nanocrystalline drug/surface modifier complex prepared as described above further comprises a cryoprotectant, for example a carbohydrate or sugar alcohol, in an amount sufficient to permit the nanoparticles to be lyophilized, substantially as described in above-cited U.S. Pat. No. 5,302,401. A preferred cryoprotectant of this embodiment is sucrose. The method of making nanoparticles having a surface modifier adsorbed on the surface thereof and a cryoprotectant associated therewith comprises contacting the nanoparticles with the cryoprotectant for a time and under conditions sufficient to permit lyophilization of the nanoparticles.

In another related embodiment of the invention, nanoparticulate drug particles having a surface modifying agent adsorbed on the surface thereof in an amount sufficient to maintain a weight average particle size of less than about 400 nm are prepared by a process comprising the steps of (a) dispersing the drug in a liquid dispersion medium wherein the drug is insoluble; and (b) grinding the medium (e.g., in a dispersion mill) in the presence of rigid grinding media, wherein pH of the medium is maintained within a range of about 2 to about 6, substantially as disclosed in above-cited U.S. Pat. No. 5,552,160.

In another related embodiment of the invention, nanoparticles are prepared by a process comprising the steps of (a) providing a selective COX-2 inhibitory drug substance; (b)

depyrogenating rigid grinding media, for example in an oven at about 200° C. to about 300° C. for about 6 to about 20 hours; mixing the drug substance and grinding media together and autoclaving at about 100° C. to about 150° C. for about 10 to about 60 minutes); and (c) adding a surface modifying agent (e.g., selected from polymers, low molecular weight oligomers, natural products and surfactants) to the resulting autoclaved drug substance followed by wet grinding to provide and maintain a weight average particle size of less than about 400 nm, substantially as disclosed in above-cited U.S. Pat. No. 5,534,270.

In another related embodiment of the invention, nanoparticles are prepared by a process comprising contacting a selective COX-2 inhibitory drug with a surface modifying agent (e.g., by adding the drug to a liquid medium comprising the surface modifying agent and wet grinding in a dispersion mill) for a time and under conditions sufficient to provide and maintain a weight average particle size of less than about 400 nm, substantially as described in above-cited U.S. Pat. No. 5,429,824. In this embodiment the surface modifying agent is a nonionic liquid polymer of the alkylaryl polyether alcohol type, for example tyloxapol. Optionally an additional surface modifying agent can be present.

In another related embodiment of the invention, nanoparticles are prepared by a process comprising the steps of (a) forming a premix of a selective COX-2 inhibitory drug and a surface modifier (e.g., selected from polymers, low molecular weight oligomers, surfactants, etc.) in a liquid dispersion medium (e.g., water, salt solution, ethanol, etc.); (b) transferring the premix to a microfluidizer having an interaction chamber capable of producing shear, impact, cavitation and attrition forces; (c) subjecting the premix to these forces at a temperature not exceeding about 40° C. and a fluid pressure of about 20,000 to about 200,000 kPa by passing the premix through the interaction chamber to reduce the particle size of the drug and to obtain a homogeneous slurry thereof; (d) collecting the slurry from the interaction chamber into a receiving tank; (e) reintroducing the slurry into the interaction chamber to further reduce particle size; and (f) repeating the collection and reintroduction steps until the weight average particle size of the drug is less than about 400 nm, substantially as disclosed in above-cited U.S. Pat. No. 5,510,118.

In another related embodiment of the invention, nanoparticles are prepared by a process comprising the steps of (a) milling (e.g., in a dispersion mill), optionally in the presence of an oil, a selective COX-2 inhibitory drug in the presence of surface modifying agents (e.g., gelatin, casein, lecithin, polyvinylpyrrolidone, tyloxapol, poloxamers, other block polymers, etc.) substantially as disclosed in above-cited U.S. Pat. No. 5,560,931. In this embodiment, the drug particles have a non-crosslinked modifier adsorbed on the surface thereof, and are suspended in an aqueous phase which is emulsified in a continuous oil phase. Weight average particle size is less than about 1000 nm. The oil phase can be oleic acid, as disclosed in above-cited U.S. Pat. No. 5,571,536.

In another related embodiment of the invention, nanoparticles are prepared by a process comprising the steps of (a) introducing a selective COX-2 inhibitory drug, a liquid medium, grinding media and a surface modifying agent into a grinding vessel; and (b) wet grinding to reduce the weight average particle size of the drug to less than about 1000 nm, substantially as disclosed in above-cited U.S. Pat. No. 5,565,188 (block copolymer as surface modifying agent containing one or more polyoxyethylene blocks and one or more polyoxy(higher alkylene) blocks wherein at least some of the blocks are linked together by an oxymethylene linking group) and U.S. Pat. No. 5,587,143 (block copolymer of ethylene oxide and butylene oxide as surface modifying agent).

In another related embodiment of the invention, a composition is provided comprising nanoparticulate selective COX-2 inhibitory drug particles having a block copolymer linked to at least one anionic group as a surface modifying agent adsorbed on the surface thereof. The composition is prepared by a process comprising the steps of (a) preparing the drug in particulate form, preferably at a particle size less than about 100 μm; (b) adding the drug to a liquid medium in which it is essentially insoluble to form a premix; and (c) subjecting the premix to mechanical means to reduce the average particle size in the premix to less than about 1000 nm, substantially as disclosed in above-cited U.S. Pat. No. 5,569,448. Preferably, the surface modifying agent is present in the premix.

In another related embodiment of the invention, nanoparticles are prepared by a process comprising the steps of (a) adding a selective COX-2 inhibitory drug and a surface modifying agent (e.g., a steric stabilizer such as gelatin, casein, lecithin, gum acacia, cholesterol, tragacanth, sorbitan esters, polyethylene glycol, polyoxyethylene alkyl esters, polyoxyethylene stearates, etc.) to a liquid in which the drug is insoluble to form a premix, and (b) subjecting the premix to mechanical means (e.g., in a dispersion mill) to reduce average particle size to less than about 400 nm, substantially as disclosed in above-cited U.S. Pat. No. 5,573,783.

In another related embodiment of the invention, nanoparticles are prepared by a process comprising the steps of (a) dispersing a selective COX-2 inhibitory drug and a surface active agent (e.g., poloxamers having a molecular weight of about 1,000 to about 15,000 daltons, polyvinyl alcohol, polyvinylpyrrolidone, hydroxypropylmethylcellulose, and polyoxyethylene sorbitan monooleate) in a liquid dispersion medium in which the drug is poorly soluble, then applying mechanical means (e.g., in a dispersion mill) to reduce drug particle size to less than about 400 nm, substantially as disclosed in above-cited U.S. Pat. No. 5,585,108.

In another related embodiment of the invention, nanoparticles are prepared by a process comprising the steps of (a) adding a selective COX-2 inhibitory drug and hydroxypropylcellulose as a surface modifying agent to a liquid medium in which the drug is essentially insoluble to form a premix, and employing mechanical means (e.g., in a dispersion mill) to reduce drug particle size to less than about 1000 nm, preferably less than about 400 nm, substantially as disclosed in above-cited U.S. Pat. No. 5,591,456.

In another related embodiment of the invention, nanoparticles are prepared by a process as described herein that employs a surface modifying agent, the surface modifying agent being selected such that the resulting composition has a hydrophile-lipophile balance (HLB) of about 4 to about 9, substantially as disclosed in above-cited International Patent Publication No. WO 00/30615.

In another particular embodiment of the invention, nanoparticles are prepared by a process comprising the steps of (a) mixing a selective COX-2 inhibitory drug with a support material, preferably a crosslinked, water-swellable polymer; (b) grinding the resulting mixture in a grinding chamber which is saturated with a solvent vapor (e.g., water, ethanol, isopropanol, chloroform, methanol, etc.); (c) drying the ground mixture under vacuum; and (d) sieving the dried ground mixture to eliminate any aggregates formed, substantially as disclosed in above-cited U.S. Pat. No. 5,354,560.

In another particular embodiment of the invention, nanoparticles are prepared by a process comprising the steps of (a) forming a paste comprising (i) nanoparticles of a selective COX-2 inhibitory drug, (ii) at least one thickening or binding agent (e.g., selected from polypeptides, high molecular weight polymers, colloids, etc.) and/or extender, (iii) one or more stabilizing agents to prevent settling and/or rising to the surface of the nanoparticles, and (iv) a suitable amount of water to adjust viscosity; and (b) lyophilizing the paste, substantially as disclosed in above-cited U.S. Pat. No. 5,384,124.

In another particular embodiment of the invention, nanoparticles are prepared by a process comprising the steps of (a) preparing a selective COX-2 inhibitory drug in particulate form, preferably at a particle size smaller than about 100 μm; (b) adding the prepared drug to a liquid medium (preferably comprising a surface modifying agent such as a hygroscopic sugar) in which the drug is essentially insoluble to form a premix; and (c) subjecting the premix to mechanical means to reduce the average particle size in the premix to less than about 1000 nm, substantially as disclosed in above-cited U.S. Pat. No. 5,518,738. Preferably, polyvinylpyrrolidone and/or a wetting agent, e.g., sodium lauryl sulfate, are also present in the premix. Compositions prepared by this process preferably have a film adsorbed on the surface of the nanoparticles comprising a polyvinylpyrrolidone, a hygroscopic sugar and sodium lauryl sulfate.

In another particular embodiment of the invention, nanoparticles are prepared by a process comprising the steps of (a) co-solubilizing one or more polymeric constituents including, for example, a biodegradable polymer (e.g., polylactic acid, polyglycolic acid or co-polymers thereof, polyhydroxybutyric acid, polycaprolactone, polyorthoesters, etc.), a polysaccharide jellifying and/or bioadhesive polymer, and/or an amphiphilic polymer (e.g. polyethylene glycol, polyvinylpyrrolidone or polyvinyl alcohol) together with an agent modifying interface properties to form a polymer mixture, optionally in the presence of one or more solvents; (b) dissolving or suspending a selective COX-2 inhibitory drug in the polymer mixture; and (c) forming particles consisting of the polymers, the agent modifying the interface properties and the drug by a technique of emulsion, extrusion, spray drying or spray congealing, substantially as disclosed in above-cited U.S. Pat. No. 5,536,508. Nanoparticles prepared by this process preferably have a weight average particle size of about 0.1 μm to about 150 μm.

In another particular embodiment of the invention, nanoparticles are prepared by a process comprising the steps of (a) preparing a solution of a selective COX-2 inhibitory drug in a water-miscible organic solvent; (b) infusing an aqueous precipitating liquid (e.g., water, solution of mineral salt, or surfactant solution) into the solution to produce a suspension of precipitated, amorphous, solid drug in the form of non-aggregated particles; and (c) separating the particles from the precipitating liquid and washing in an aqueous washing liquid, substantially as disclosed in above-cited U.S. Pat. No. 4,826,689.

In another particular embodiment of the invention, nanoparticles are prepared by a process comprising the steps of (a) dissolving a selective COX-2 inhibitory drug in an aqueous base (e.g., NaOH, KOH, CsOH, etc.) with stirring to form a solution; (b) adding a surface modifier (e.g., various polymers, surfactants, low molecular weight oligomers, etc.) to form a clear solution; and (c) neutralizing the clear solution with stirring and with an appropriate acid solution (e.g., HCl, HNO$_3$, HClO$_4$, H$_2$SO$_4$, formic acid, propionic acid, acetic acid, butyric acid, etc.), substantially as disclosed in above-cited U.S. Pat. No. 5,560,932 and No. 5,580,579.

In another related embodiment of the invention, nanoparticles are prepared by a process comprising the steps of (a) dissolving a selective COX-2 inhibitory drug in a liquid medium base (e.g., NaOH, KOH, CsOH, trialkylamines, pyridine, etc.) comprising a non-toxic solvent in which the drug is poorly soluble to form a solution; (b) adding an aqueous solution of one or more surface modifying agents (e.g., anionic or nonionic surfactants, polymeric or oligomeric substances); and (c) neutralizing the resulting alkaline solution with an acid (e.g., HCl, HNO$_3$, HClO$_4$, H$_2$SO$_4$, formic acid, propionic acid, acetic acid, butyric acid, etc.), to form a dispersion, preferably having a Z-average particle diameter of less than about 100 nm as measured by photon correlation spectroscopy, substantially as disclosed in above-cited U.S. Pat. No. 5,662,883.

In another related embodiment of the invention, nanoparticles are prepared by a process comprising the steps of (a) dissolving a selective COX-2 inhibitory drug and a crystal growth modifier (i.e., a compound that is substantially isostructural to the drug) in an aqueous base (e.g., NaOH, KOH, CsOH, trialkylamines, pyridine, etc.) to form a solution; (b) adding an aqueous solution of one or more surface modifying agents (e.g., a mixture of anionic surfactant, nonionic surfactant, polymeric substance and oligomeric substance); and neutralizing the resulting alkaline solution with an acid (e.g., HCl, HNO$_3$, HClO$_4$, H$_2$SO$_4$, formic acid, propionic acid, acetic acid, butyric acid, etc.), to form a dispersion, preferably wherein the drug particles have a Z-average particle diameter of less than about 400 nm as measured by photon correlation spectroscopy, substantially as disclosed in above-cited U.S. Pat. No. 5,665,331.

In another particular embodiment of the invention, nanoparticles having a weight average particle size of less than about 400 nm are prepared from a dispersion comprising a first particle distribution of a selective COX-2 inhibitory drug together with a surface modifying agent such as polysulfated tyloxapol by a process comprising the steps of (a) placing the dispersion between a first electrode and a second electrode; and (b) removing a portion of the dispersion at a position between the first electrode and the second electrode, this portion of the dispersion having a second particle size distribution that is smaller than the first particle distribution, substantially as disclosed in above-cited U.S. Pat. No. 5,503,723.

In another particular embodiment of the invention, nanoparticles having a weight average particle size of up to about 300 nm are prepared by a process comprising the steps of (a) dissolving a selective COX-2 inhibitory drug in a solvent to form a solution; and (b) spraying the solution into a liquefied gas or supercritical fluid in presence of a surface modifying agent dispersed or dissolved in an aqueous phase, substantially as disclosed in above-cited International Patent Publication No. WO 97/14407.

In another related embodiment of the invention, nanoparticles having a weight average particle size of up to about 300 nm are prepared by a process comprising the steps of (a) dissolving a selective COX-2 inhibitory drug in a liquefied gas or supercritical fluid to form a solution; (b) preparing an aqueous phase containing a surface modifying agent; and (c) spraying the solution into the aqueous phase, substantially as disclosed in the same above-cited International Patent Publication No. WO 97/14407.

In another related embodiment of the invention, nanoparticles are prepared by a process comprising the steps of (a)

dissolving a selective COX-2 inhibitory drug and a surface modifying agent in a liquefied gas or supercritical fluid to form a solution; and (b) expanding the solution into an aqueous medium, substantially as disclosed in above-cited International Patent Publication No. WO 99/13755.

Excipients included in a composition of the invention can be solids or liquids or both. Compositions of the invention containing excipients can be prepared by any technique of pharmacy that comprises admixing the excipients with a selective COX-2 inhibitory drug that has been at least partially pre-prepared, optionally together with one or more excipients, in nanoparticulate form as indicated above.

Compositions suitable for buccal or sublingual administration include, for example, lozenges comprising the selective COX-2 inhibitory drug in a flavored base, such as sucrose and acacia or tragacanth, and pastilles comprising the drug in an inert base such as gelatin and glycerin or sucrose and acacia.

Liquid dosage forms for oral administration include pharmaceutically acceptable suspensions, syrups, and elixirs containing inert diluents commonly used in the art, such as water. Such compositions may also comprise, for example, wetting agents, emulsifying and suspending agents, and sweetening, flavoring, and perfuming agents.

Solid unit dosage forms for oral administration contain the selective COX-2 inhibitory drug in nanoparticulate form together with excipients and are most conveniently formulated as tablets or capsules. Non-limiting examples follow of excipients that can be used to prepare pharmaceutical compositions of the invention.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility.

Lactose and microcrystalline cellulose, either individually or in combination, are preferred diluents. Both diluents are chemically compatible with celecoxib. The use of extragranular microcrystalline cellulose (that is, microcrystalline cellulose added to a wet granulated composition after a drying step) can be used to improve hardness (for tablets) and/or disintegration time. Lactose, especially lactose monohydrate, is particularly preferred. Lactose typically provides compositions having suitable release rates of celecoxib, stability, pre-compression flowability, and/or drying properties at a relatively low diluent cost. It provides a high density substrate that aids densification during granulation (where wet granulation is employed) and therefore improves blend flow properties.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition.

Croscarmellose sodium is a preferred disintegrant for tablet or capsule disintegration, and, if present, preferably constitutes about 0.2% to about 10%, more preferably about 0.2% to about 7%, and still more preferably about 0.2% to about 5%, of the total weight of the composition. Croscarmellose sodium confers superior intragranular disintegration capabilities to granulated compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, preferably about 0.75% to about 15%, and more preferably about 1% to about 10%, of the total weight of the composition.

Compositions of the invention optionally comprise one or more pharmaceutically acceptable wetting agents as excipients. Such wetting agents are preferably selected to maintain the selective COX-2 inhibitory drug in close association with water, a condition that is believed to improve bioavailability of the composition.

Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the composition.

Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium, calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition.

Magnesium stearate is a preferred lubricant used, for example, to reduce friction between the equipment and granulated mixture during compression of tablet formulations.

Suitable anti-adherents include talc, cornstarch, DL-leucine, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition.

Other excipients such as colorants, flavors and sweeteners are known in the pharmaceutical art and can be used in compositions of the present invention. Tablets can be coated, for example with an enteric coating, or uncoated. Compositions of the invention can further comprise, for example, buffering agents.

Optionally, one or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70%, for example about 60%, by weight of the composition.

In one embodiment of the invention, the composition is in the form of unit dose capsules or tablets and comprises a partially or wholly nanoparticulate selective COX-2 inhibitor, illustratively celecoxib, in a desired amount together with one or more excipients selected from the group consisting of pharmaceutically acceptable diluents, disintegrants, binding agents, wetting agents and lubricants. More preferably, the composition comprises one or more excipients selected from the group consisting of lactose (most preferably lactose monohydrate), sodium lauryl sulfate, polyvinylpyrrolidone, croscarmellose sodium, magnesium stearate and microcrystalline cellulose. Still more preferably, the composition comprises lactose monohydrate and croscarmellose sodium. Even more preferably, such a composition further comprises one or more of the carrier materials sodium lauryl sulfate, magnesium stearate and microcrystalline cellulose.

Excipients for capsule and tablet compositions of the invention are preferably selected to provide a disintegration time of less than about 30 minutes, preferably about 25 minutes or less, more preferably about 20 minutes or less, and still more preferably about 15 minutes or less, in a standard disintegration assay.

Illustratively for tablet formulations, a complete blend of ingredients in an amount sufficient to make a uniform batch of tablets is subjected to tableting in a conventional production scale tableting machine at normal compression pressure (for example, applying a force of about 1 kN to about 50 kN in a typical tableting die). Any tablet hardness convenient with respect to handling, manufacture, storage and ingestion can be obtained. For 100 mg tablets, hardness is preferably at least 4 kP, more preferably at least about 5 kP, and still more preferably at least about 6 kP. For 200 mg tablets, hardness is preferably at least 7 kP, more preferably at least about 9 kP, and still more preferably at least about 11 lkP. The mixture, however, is not to be compressed to such a degree that there is subsequent difficulty in achieving hydration when exposed to gastric fluid.

Tablet friability is preferably less than about 1.0%, more preferably less than 0.8%, and still more preferably less than about 0.5% in a standard test.

Wet granulation, dry granulation or direct compression or encapsulation methods can be employed to prepare tablet or capsule compositions of the invention.

Although unit dose capsule and tablet compositions of the invention can be prepared, for example, by direct encapsulation or direct compression, they are preferably wet granulated prior to encapsulation or compression. Wet granulation, among other effects, densifies milled compositions resulting in improved flow properties, improved compression characteristics and easier metering or weight dispensing of the compositions for encapsulation or tableting. The secondary particle size resulting from granulation (i.e., granule size) is not narrowly critical, it being important only that the average granule size preferably is such as to allow for convenient handling and processing and, for tablets, to permit the formation of a directly compressible mixture that forms pharmaceutically acceptable tablets.

In an illustrative wet granulation process, any portion of the drug that is not to be included in nanoparticulate form (if desired, together with one or more carrier materials) is initially milled or micronized to a desired range of particle sizes greater than 1 μm. Although various conventional mills or grinders can be used, impact milling such as pin milling of the drug provides improved blend uniformity to the final composition relative to other types of milling. Cooling of the material being milled, for example, using liquid nitrogen, may be necessary during milling to avoid heating the drug to undesirable temperatures. The $D_{90}$ particle size during this milling step is preferably reduced to less than about 25 μm.

The milled or micronized drug, if any, is then blended with the desired amount of nanoparticulate drug, prepared as indicated hereinabove to provide a partially or wholly nanoparticulate drug substance. Simultaneously or thereafter, the drug substance is blended, for example in a high shear mixer/granulator, planetary mixer, twin-shell blender or sigma mixer, with one or more excipients, including excipients that have been milled together with the celecoxib or are present in the nanoparticles, to form a dry powder mixture. Typically, the drug substance is blended with one or more diluent(s), disintegrant(s) and/or binding agent(s) and, optionally, one or more wetting agent(s) in this step, but alternatively all or a portion of one or more of the excipients can be added in a later step. For example, in tablet formulations where croscarmellose sodium is employed as a disintegrant, it has been discovered that addition of a portion of the croscarmellose sodium during the blending step (providing intragranular croscarmellose sodium) and addition of the remaining portion after the drying step discussed below (providing extragranular croscarmellose sodium) can improve disintegration of the tablets produced. In this situation, preferably about 60% to about 75% of the croscarmellose sodium is added intragranularly and about 25% to about 40% of the croscarmellose sodium is added extragranularly. Similarly, for tablet formulations it has been discovered that addition of microcrystalline cellulose after the drying step below (extragranular microcrystalline cellulose) can improve compressibility of the granules and hardness of tablets prepared from the granules.

This blending step of the process preferably comprises blending of drug substance, lactose, polyvinylpyrrolidone and croscarmellose sodium. It has been discovered that a blending time as short as three minutes can provide a dry powder mixture having a sufficiently uniform distribution of the drug to provide a commercially acceptable tablet.

Water, preferably purified water, is then added to the dry powder mixture and the mixture is blended for an additional period of time, to form a wet granulated mixture. Preferably a wetting agent is used, and this is preferably first added to the water and mixed for at least 15 minutes, preferably at least 20 minutes, prior to adding the water to the dry powder mixture. The water can be added to the mixture at once, gradually over a period of time, or in several portions over a period of time. The water is preferably added gradually over a period of time. Alternatively, the wetting agent can be added to the dry powder mixture and water can then be added to the resulting mixture. An additional period of mixing after water addition is complete is preferred to ensure uniform distribution of water in the mixture.

The wet granulated mixture is preferably then wet milled, for example with a screening mill, to eliminate large agglomerates of material that form as a by-product of the wet granulation operation. If not removed, these agglomerates would prolong the subsequent drying operation and increase variation with respect to moisture control.

The wet granulated or wet milled mixture is then dried, for example, in an oven or a fluid bed dryer, preferably a fluid bed drier, to form dry granules. If desired, the wet granulated mixture can be extruded or spheronized prior to drying. For the drying process, conditions such as inlet air temperature and drying time are adjusted to achieve the desired moisture content for the dry granules. It may be desirable to combine two or more granulation sections for this drying step and subsequent processing steps.

To the extent necessary, the dry granules are then reduced in size in preparation for compression or encapsulation. Conventional particle size reduction equipment such as oscillators or impact mills (such as Fitz mills) can be employed.

A slight decrease in granule size has been observed as mixing time increases for mixtures containing lower water amounts. It is hypothesized that where water concentration is too low to fully activate the binding agent employed, cohesive forces between the primary particles within the granules are insufficient to survive the shearing forces generated by the mixing blades and granule size attrition rather than growth occurs. Conversely, increasing the amount of water to fully activate the binding agent allows cohesive forces between the primary particles to survive the shearing forces generated by the mixing blades and granule growth rather than attrition occurs with increased mixing time and/or water addition rate. Variation of the screen size of the wet mill tends to have a greater impact on the granule size than variation of the feed rate and/or mill speed.

The dry granules are then placed in a suitable blender, such as a twin-shell blender, and optionally a lubricant (such as magnesium stearate) and any additional carrier materials are added (such as extragranular microcrystalline cellulose and/or extragranular croscarmellose sodium in certain tablet formulations) to form a final blended mixture. Where the diluents include microcrystalline cellulose, the addition of a portion of the microcrystalline cellulose during this step has been found to materially increase granule compressibility and tablet hardness. However, increasing the amount of magnesium stearate above about 1% to about 2% tends to decrease tablet hardness and increase friability and dissolution time.

This final blended mixture is then encapsulated (or, if tablets are to be prepared, compressed into tablets of the desired weight and hardness using appropriately sized tooling). Conventional compression and encapsulation techniques known in the art can be employed. Suitable results are obtained for capsules by employing bed heights ranging from about 20 mm to about 60 mm, compaction settings ranging from about 0 to about 5 mm, and speeds from about 60,000 capsules per hour to about 130,000 capsules per hour. Slug formation can be minimized or eliminated by using the lowest compaction setting at which capsule weight control can be maintained. Where coated tablets are desired, conventional coating techniques known in the art can be employed.

This combination of operations produces granules that are uniform in drug content at the unit dose level, that readily disintegrate, that flow with sufficient ease so that weight variation can be reliably controlled during capsule filling or tableting, and that are dense enough in bulk so that the batch can be processed in the selected equipment and individual doses fit into the specified capsules or tablet dies.

The present invention is also directed to use of compositions of the invention in preparation of medicaments useful in treatment and/or prophylaxis of COX-2 mediated conditions and disorders, in particular such conditions and disorders where rapid onset of therapeutic effect is desired or required.

DESCRIPTION OF A PARTICULARLY PREFERRED EMBODIMENT

Patent and other literature relating to nanoparticulate drug compositions teaches that, in general, the smaller the drug particle size, the greater is the advantage in speed of onset of therapeutic effect, or other pharmacodynamic benefit, obtained upon oral administration. For example, at least the following patents propose reduction of particle size to about 400 nm or smaller.

Above-cited U.S. Pat. No. 5,145,684.
Above-cited U.S. Pat. No. 5,298,262.
Above-cited U.S. Pat. No. 5,302,401.
Above-cited U.S. Pat. No. 5,336,507.
Above-cited U.S. Pat. No. 5,340,564.
Above-cited U.S. Pat. No. 5,346,702.
Above-cited U.S. Pat. No. 5,352,459.
Above-cited U.S. Pat. No. 5,429,824.
Above-cited U.S. Pat. No. 5,503,723.
Above-cited U.S. Pat. No. 5,510,118.
Above-cited U.S. Pat. No. 5,534,270.
Above-cited U.S. Pat. No. 5,552,160.
Above-cited U.S. Pat. No. 5,573,783.
Above-cited U.S. Pat. No. 5,585,108.
Above-cited U.S. Pat. No. 5,591,456.
Above-cited U.S. Pat. No. 5,662,883.
Above-cited U.S. Pat. No. 5,665,331.

In general, however, the smaller the drug particle size, the more grinding or milling time, energy and labor is required to produce the particles and consequently, the more costly and less efficient is the process. Thus, smaller nano-sized drug particles are generally significantly more expensive and labor-intensive to produce in quantity than larger nano-sized drug particles.

Surprisingly, we have now discovered that a selective COX-2 inhibitory drug composition having a weight average particle size of about 450 nm to about 1000 nm (referred to herein as a "sub-micron" formulation and particle size) exhibits onset time and bioavailability substantially equal to that of a comparative composition having a weight average particle size of about 200 to about 400 nm, as measured in vitro and in vivo. The sub-micron formulation requires less milling time and energy than the formulation comprising smaller nanoparticles with a weight average particle size in the 200–400 nm range.

It is further contemplated that certain advantages in addition to cost saving are obtainable with sub-micron as opposed to smaller particle sizes. For example, in situations where ultra-fine particles tend to agglomerate or fail to disperse in the gastrointestinal fluid, the slightly larger sub-micron particles can exhibit enhanced dispersion.

Accordingly, in a particularly preferred embodiment of the present invention, there is provided a pharmaceutical composition comprising one or more orally deliverable dose units, each comprising a selective COX-2 inhibitory drug of low water solubility in a therapeutically effective amount, wherein the drug is present in solid particles having a $D_{25}$ particle size of about 450 nm to about 1000 nm, and more preferably about 500 nm to about 900 nm, the composition providing at least a substantially similar $C_{max}$ and/or at most a substantially similar $T_{max}$ by comparison with an otherwise similar composition having a $D_{25}$ particle size of less than 400 nm, and/or providing a substantially greater $C_{max}$ and/or a substantially shorter $T_{max}$ by comparison with an otherwise similar composition having a $D_{25}$ particle size larger than 1000 nm.

There is also provided a pharmaceutical composition comprising one or more orally deliverable dose units, each comprising a selective COX-2 inhibitory drug of low water solubility in a therapeutically effective amount, wherein the drug is present in solid particles, about 25% to 100% by weight of which have a particle size of about 450 nm to about 1000 nm, more preferably about 500 nm to about 900 nm.

There is also provided a pharmaceutical composition comprising one or more orally deliverable dose units, each comprising a selective COX-2 inhibitory drug of low water solubility in a therapeutically effective amount, wherein the drug is present in solid particles having a weight average particle size of about 450 nm to about 1000 nm, and more preferably about 500 nm to about 900 nm, the composition providing at least a substantially similar $C_{max}$ and/or at most a substantially similar $T_{max}$ by comparison with an otherwise similar composition having a weight average particle size of less than 400 nm, and/or providing a substantially greater $C_{max}$ and/or a substantially shorter $T_{max}$ by comparison with an otherwise similar composition having a weight average particle size larger than 1000 nm. For purposes of this description, "weight average particle size" can be considered synonymous with $D_{50}$ particle size.

Sub-micron particles of a selective COX-2 inhibitory drug can be prepared by modification of processes described hereinabove for preparation of nanoparticles, or by a process as illustratively set forth in Example 1 below.

EXAMPLES

Example 1

Dispersions D1–D4 containing 5% by weight celecoxib were prepared by the process described below. The dispersions differed only in the particle size range of the celecoxib.

1. Celecoxib was micronized in an air jet mill to form a drug powder.
2. The drug powder was added to an aqueous solution containing 2.5% low viscosity hydroxypropylcellulose (HPC-SL) and 0.12% sodium dodecyl sulfate, to form a suspension.
3. The suspension was wet milled to form an intermediate dispersion according to the following protocol. A sample amount of 6.0 ml of the suspension (containing 20% celecoxib), a magnetic stir bar, 8 ml of lead-free glass beads, and 50 μl of antifoaming agent (Sigma Antifoam A Concentrate) were added to a 20 ml scintillation vial. To provide an intermediate dispersion having a target particle size range of 6–7 μm (i.e., the size range achieved in the micronizing step, used to provide a comparative composition), the vial was shaken for two minutes. To provide intermediate dispersions having smaller target particle size ranges, the vial was suspended over a high-strength rotating magnet so that milling occurred by agitation of the glass beads by rotation of the magnetic stir bar. Target particle size ranges were varied by controlling magnet rotation rate, milling time and/or bead size, as shown in Table 1. Small aliquots were removed at intervals in order to monitor progress of particle size reduction.
4. The resulting intermediate dispersion in each case was transferred to a larger vial and diluted with fresh vehicle to form a final dispersion. Nominal celecoxib concentration in the final dispersions was 5% by weight.

TABLE 1

Milling conditions used to produce celecoxib dispersions D1–D4.

| Dispersion | Target size range (μm) | Bead size (mm) | Milling time (min) | Milling speed (rpm) |
|---|---|---|---|---|
| D1 | 6–7 | 3.3–3.6 | — | — |
| D2 | 1–3 | 3.3–3.6 | 26 | 900 |

TABLE 1-continued

Milling conditions used to produce celecoxib dispersions D1–D4.

| Dispersion | Target size range (μm) | Bead size (mm) | Milling time (min) | Milling speed (rpm) |
|---|---|---|---|---|
| D3 | 0.5–0.9 | 1.25–1.55 | 25 | 900 |
| D4 | 0.2–0.4 | 0.5 | 52 | 1250 |

Example 2

Celecoxib particle size in dispersions D1–D4 as prepared in Example 1 was determined by laser (Fraunhofer) diffraction and by optical microscopy.

Fraunhofer scattering was measured on static dispersion samples using a Sympatec spectrometer. Samples were diluted with water into a static cell at a concentration that maintained a reduction in laser intensity of approximately 20%. The choice of collection lens was determined by the population of large material present in suspension, and thus was different for each sample. However, the smallest focal length optic appropriate was used in each case. No Mie scattering corrections were applied. The results, presented in FIG. 1, show a $D_{50}$ particle size consistent with the target size range. $D_{50}$ and other particle size parameters shown in FIG. 1 are believed to be overestimated for the 0.2–0.4 μm celecoxib dispersion, since this size range is at the very limit of detection by this technique.

Figure 2:
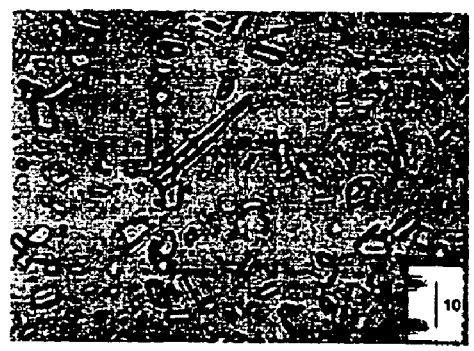
FIG. 2 shows optical micrographs of samples taken from dispersions D1–D4 under non-polarized (left) and polarized (right) light.
Figure 2:
Figure 2:
Figure 2:
Figure 2:
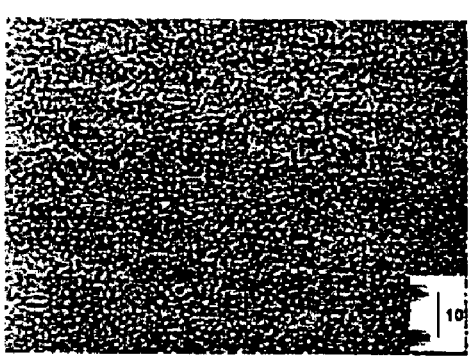
Figure 2:
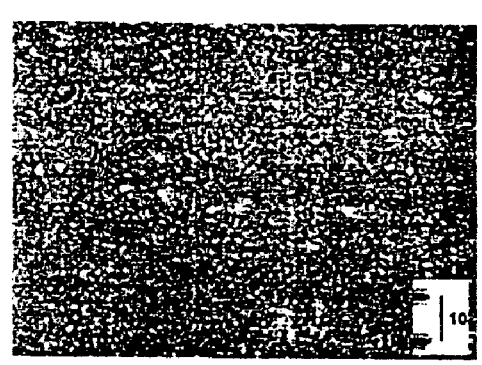
Figure 2:
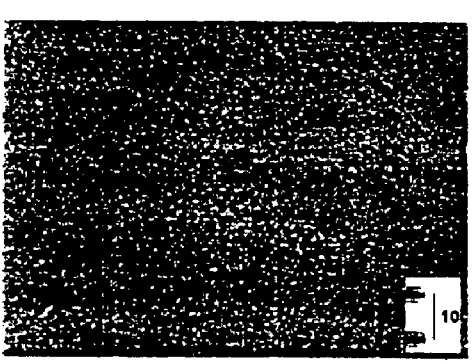
Figure 2:

In order to visually confirm particle sizes, optical microscopy was used. Observations were carried out using an Olympus BH-2 microscope with attached video camera. Images were then digitized (Snappy 4.0; Play Inc., Rancho Cordova, Calif.) and manipulated (Paint Shop Pro 6.02; JASC, Eden Prairie, Minn.) as appropriate. FIG. 2 shows micrographs of samples taken from celecoxib dispersions D1–D4 with non-polarized (left) and polarized (right) light. The bar represents 10 μm. Significant Brownian motion was observed in dispersions D3 and D4, an observation consistent with presence of very small nanoparticles. In contrast, only slight Brownian motion was noted in dispersion D2 and none at all in dispersion D1.

Example 3

Figure 4:
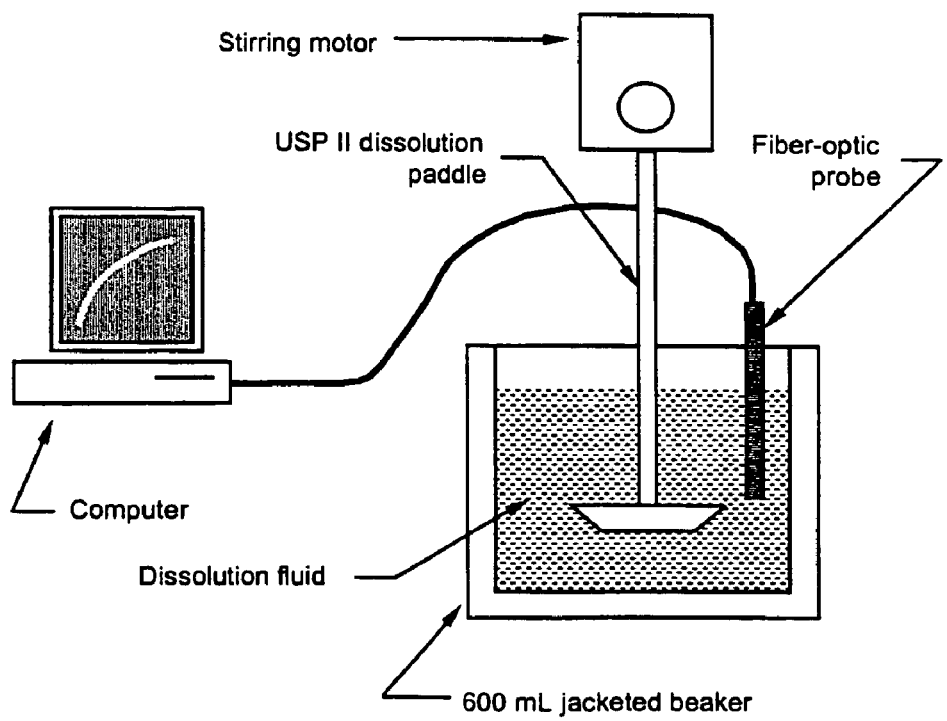
FIG. 4 is a schematic representation of apparatus used to perform the in vitro dissolution assay of Example 3.

Dissolution characteristics of celecoxib crystals in dispersions D1–D4 of Example 1 were evaluated in an in vitro dissolution assay performed as described below. FIG. 4 is a schematic representation of the apparatus used in this experiment. The dissolution vessel is a 600 ml jacketed beaker. The jacket is connected to a temperature-controlled water circulator, which serves to maintain the temperature of the dissolution fluid at 37° C. A standard USP II dissolution paddle is utilized to stir the dissolution fluid. The paddle is driven by a computer-controlled constant-velocity motor, which is set to operate at 75 rpm throughout the course of the assay.

Dispersion samples are injected into the dissolution vessel just below the surface of the dissolution fluid. A sample is introduced in this way to minimize likelihood that particles become trapped on the surface of the fluid. Simultaneously, a data acquisition program is initiated. A sample point is taken at 30 seconds and then every 30 seconds thereafter for the duration of the assay. Dissolution progress is then followed for 60 minutes for each sample studied. The concentration of dissolved drug in the vessel is monitored via an in situ fiber-optic probe, which measures the optical absorbance of dissolved drug in the dissolution fluid. The probe remains submerged in the fluid throughout the course of the assay. The concentration of dissolved drug in the fluid is determined from the measured absorbance values according to the Beer-Lambert equation $$c = \frac{A}{l \cdot \varepsilon}$$

where A is the measured absorbance at 254 nm, l is the path length of the probe in cm, $\varepsilon$ is the absorption coefficient at 254 nm in ml/(μg.cm), and c is drug concentration in μg/ml. The path length of the fiber-optic probe is fixed at 1 cm. A typical calibration procedure using a standard solution of celecoxib is used to determine the absorption coefficient at 254 nm.

An attached personal computer is configured to record an absorbance value every 30 seconds. Thus an experimental data set consists of in situ absorbance values at 30-second intervals for the entire course of the experiment. The absorbance values are then converted to drug concentration via the Beer-Lambert equation above.

Prior to analyzing dispersions of the invention, a dissolution vessel was filled with 500 ml of dissolution fluid (deionized water), and allowed to equilibrate to 37° C. A dissolution paddle and fiber-optic probe were placed into the vessel and also allowed to equilibrate to 37° C. Celecoxib dispersions D1–D4 prepared as in Example 1 were sonicated for approximately 5 minutes before assay. Each dispersion was hand shaken and immediately thereafter a 40 μl sample of the dispersion was extracted with a micropipette for placement in the dissolution fluid as described above.

Figure 3:
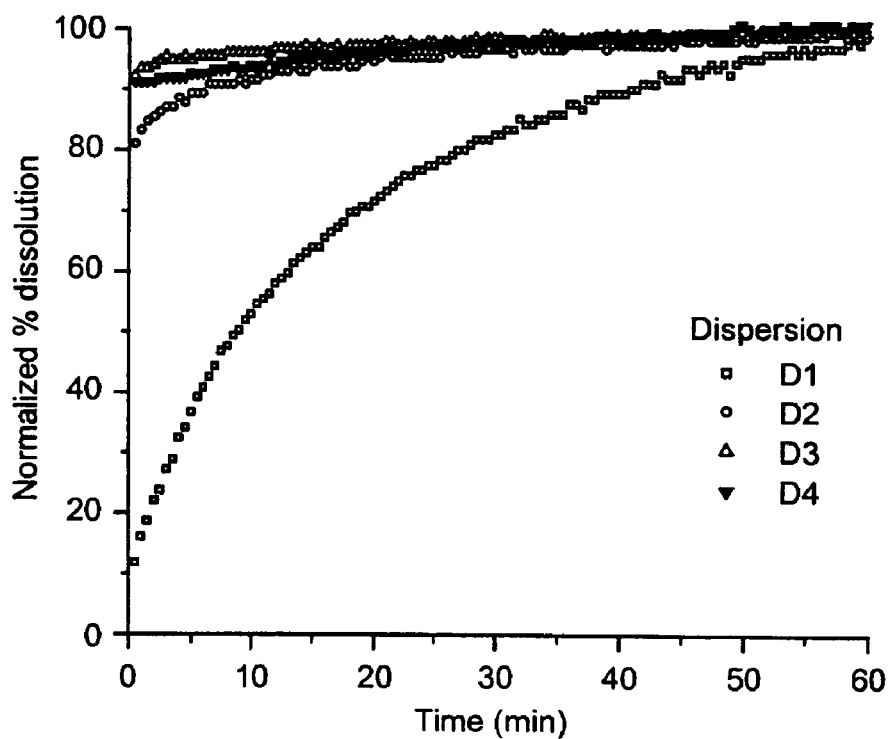
FIG. 3 shows time-course of in vitro dissolution of dispersions D1–D4.

FIG. 3 shows dissolution rates of dispersions D1–D4. To facilitate comparison, all of the dissolution traces are normalized to the same value at 60 min. This normalization step is necessary, when comparing very similar dissolution profiles, to compensate for small variations in sample volume. The plot shows the normalized percentage of celecoxib dissolved as a function of time.

Overall, comparative dispersion D1 dissolved much more slowly than did dispersions D2, D3 and D4 of the present invention, all of which dissolved at substantially similar rates. This result suggests that there is no significant functional advantage in dissolution rate to be obtained by milling celecoxib particles to a weight average particle size less than 400 nm as compared to a weight average particle size in the 450 nm to 1000 nm range. All nanoparticulate dispersions show a significant advantage in dissolution rate by comparison with the micronized celecoxib dispersion.

Example 4

Pharmacokinetic properties of celecoxib dispersions D1–D4 prepared as in Example 1 were evaluated in an in vivo dog study.

Eight male beagle dogs were given a 10 mg/kg dose of each of the four celecoxib dispersions D1–D4. Venous blood was collected pre-dose, and at 0.25, 0.5, 0.75, 1, 1.5, 2, 3, 5, 8, and 24 hours post dose. Plasma was separated from blood by centrifugation and plasma drug concentration was determined by high performance liquid chromatography. The resulting pharmacokinetic data are shown in Table 2.

TABLE 2

Pharmacokinetic parameters of celecoxib dispersions D1–D4

|  | Dipersion | | | |
| --- | --- | --- | --- | --- |
|  | D1 | D2 | D3 | D4 |
| $T_{max}$ (h) | 1.2 | 0.84 | 0.72 | 0.72 |
| $C_{max}$ (ng/ml) | 1400 | 4850 | 6120 | 6310 |
| AUC (h * ng/ml) | 14600 | 32700 | 37500 | 43500 |

$T_{max}$, $C_{max}$ and AUC (total bioavailability) values of dispersions D3 (target particle size range 0.5–0.9 μm) and D4 (target particle size range 0.2–0.4 μm) were very similar. Dispersion D2 (target particle size range 1–3 μm) exhibited slightly longer $T_{max}$ and moderately lower $C_{max}$ and AUC values than dispersions D4 and D3. $T_{max}$ of dispersion $D_1$ was much longer and $C_{max}$ and AUC were much lower than those of dispersions D2, D3 and D4.

These results suggest that where fast onset therapeutic effect is desired, good bioavailability will be obtained with celecoxib milled to a target particle size range of 0.5–0.9 μm and a $D_{50}$ particle size as determined by Fraunhofer scattering (FIG. 1) of about 0.9 μm. No significant benefit is gained by expending additional time and energy to mill celecoxib particles to a target particle size range of 0.2–0.4 μm.

What is claimed is:

1. A pharmaceutical composition, wherein:
the composition comprises one or more orally deliverable dose units, each comprising a selective cyclooxygenase-2 inhibitory drug of low water solubility in a therapeutically effective amount, wherein the drug is present in solid particles having a weight average particle size of about 500 nm to about 900 nm;
the selective cyclooxygenase-2 inhibitory drug is a compound of formula:

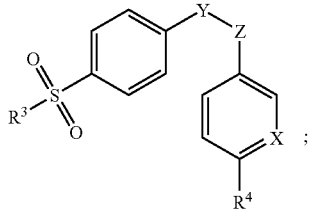

$R^3$ methyl or amino;
$R^4$ is hydrogen, $C_{1-4}$ alkyl, or $C_{1-4}$ alkoxy;
X is N or $CR^5$;
$R^5$ is hydrogen or halogen; and
Y and Z are independently carbon or nitrogen atoms defining adjacent atoms of a five- to six-membered ring that is unsubstituted or substituted at one or more positions with oxo, halo, methyl, or halomethyl.

2. The composition of claim 1 wherein the dose units are in the form of discrete solid articles.

3. The composition of claim 2 wherein the solid articles are tablets or capsules.

4. The composition of claim 1 that is in the form of a substantially homogeneous flowable mass from which single dose units are measurably removable.

5. The composition of claim 4 wherein the substantially homogeneous flowable mass is a liquid suspension.

6. The composition of claim 1 wherein Y and Z are independently carbon or nitrogen atoms defining adjacent atoms of a ring selected from the group consisting of cyclopentenone, furanone, methylpyrazole, isoxazole, and pyridine rings substituted at no more than one position.

7. The composition of claim 1 wherein the selective cyclooxygenase-2 inhibitory drug is selected from the group consisting of celecoxib, deracoxib, valdecoxib, rofecoxib, 5-chloro-3-(4-methylsulfonyl)phenyl-2-(2-methyl-5-pyridinyl)pyridine, 2-(3,5-difluorophenyl)-3-[4-(methylsulfonyl) phenyl]-2-cyclopenten-1-one and (S)-6,8-dichloro-2-(trifluoromethyl)-2H-1-benzopyran-3-carboxylic acid.

8. The composition of claim 7 wherein the selective cyclooxygenase-2 inhibitory drug is celecoxib.

9. The composition of claim 8 comprising about 10 mg to about 1000 mg celecoxib in each dose unit.

10. A method of treating a medical condition or disorder in a subject where treatment with a cyclooxygenase-2 inhibitor is indicated, wherein:
the method comprises orally administering one or more dose units of a composition one to about six times a day;
the composition comprises a selective cyclooxygenase-2 inhibitory drug of low water solubility in a therapeutically effective amount, wherein the drug is present in solid particles having a weight average particle size of about 500 nm to about 900 nm;
the selective cyclooxygenase-2 inhibitory drug is a compound of formula:

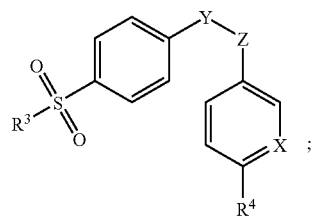

$R^3$ methyl or amino;
$R^4$ is hydrogen, $C_{1-4}$ alkyl, or $C_{1-4}$ alkoxy;
X is N or $CR^5$;
$R^5$ is hydrogen or halogen; and
Y and Z are independently carbon or nitrogen atoms defining adjacent atoms of a five- to six-membered ring that is unsubstituted or substituted at one or more positions with oxo, halo, methyl, or halomethyl.

11. The method of claim 10 wherein the medical condition or disorder is accompanied by acute pain.

12. The method of claim 10 wherein the dose units are in the form of discrete solid articles.

13. The method of claim 12 wherein the solid articles are tablets or capsules.

14. The method of claim 10 that is in the form of a substantially homogeneous flowable mass from which single dose units are measurably removable.

15. The method of claim 10 wherein Y and Z are independently carbon or nitrogen atoms defining adjacent atoms of a ring selected from the group consisting of cyclopentenone, furanone, methylpyrazole, isoxazole, and pyridine rings substituted at no more than one position.

16. The method of claim 10 wherein the selective cyclooxygenase-2 inhibitory drug is selected from the group consisting of celecoxib, deracoxib, valdecoxib, rofecoxib, 5-chloro-3-(4-methylsulfonyl)phenyl-2-(2-methyl-5-pyridinyl)pyridine, 2-(3,5-difluorophenyl)-3-[4-(methylsulfonyl)phenyl]-2-cyclopenten-1-one and (S)-6,8-dichloro-2-(trifluoromethyl)-2H-1-benzopyran-3-carboxylic acid.

17. A method of making a medicament useful in treatment or prophylaxis of a COX-2 mediated condition or disorder, wherein:

the method comprises incorporation of a selective cyclooxygenase-2 inhibitory drug of low water solubility into a pharmaceutical composition comprising one or more orally deliverable dose units, wherein the drug is in the form of solid particles having a weight average particle size of about 500 nm to about 900 nm; the selective cyclooxygenase-2 inhibitory drug is a compound of formula:

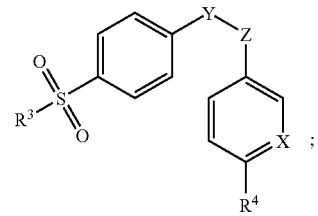

$R^3$ is methyl or amino;
$R^4$ is hydrogen, $C_{1-4}$ alkyl, or $C_{1-4}$ alkoxy;
X is N or $CR^5$;
$R^5$ is hydrogen or halogen; and
Y and Z are independently carbon or nitrogen atoms defining adjacent atoms of a five- to six-membered ring that is unsubstituted or substituted at one or more positions with oxo, halo, methyl, or halomethyl.

* * * * *

UNITED STATES PATENT AND TRADEMARK OFFICE
CERTIFICATE OF CORRECTION

PATENT NO. : 7,172,769 B2  Page 1 of 1
APPLICATION NO. : 10/031898
DATED : February 6, 2007
INVENTOR(S) : Kararli et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (467) days Delete the phrase "by 467 days" and insert -- by 211 days --

Signed and Sealed this

Thirtieth Day of September, 2008

JON W. DUDAS
*Director of the United States Patent and Trademark Office*